US009018257B2

(12) United States Patent
Rephaeli et al.

(10) Patent No.: US 9,018,257 B2
(45) Date of Patent: Apr. 28, 2015

(54) 5-AMINOLEVULINIC ACID DERIVATIVES, METHODS FOR THEIR PREPARATION AND USES THEREOF

(75) Inventors: Ada Rephaeli, Herzliya (IL); Nataly Tarasenko, Petah-Tikva (IL); Zvi Malik, Kefar Haroe (IL); Abraham Nudelman, Rehovot (IL); Gili Berkovitch-Luria, Petach-Tikva (IL); Dvir Doron, Givat Shmuel (IL)

(73) Assignees: Bar Ilan University, Ramat Gan (IL); Ramot at Tel Aviv University Ltd., Tel Aviv (IL)

( * ) Notice: Subject to any disclaimer, the term of this patent is extended or adjusted under 35 U.S.C. 154(b) by 0 days.

(21) Appl. No.: 14/007,028

(22) PCT Filed: Mar. 22, 2012

(86) PCT No.: PCT/IL2012/000127
§ 371 (c)(1),
(2), (4) Date: Sep. 24, 2013

(87) PCT Pub. No.: WO2012/127466
PCT Pub. Date: Sep. 27, 2012

(65) Prior Publication Data
US 2014/0024710 A1    Jan. 23, 2014

Related U.S. Application Data

(60) Provisional application No. 61/466,987, filed on Mar. 24, 2011, provisional application No. 61/514,053, filed on Aug. 2, 2011.

(51) Int. Cl.
| | | |
|---|---|---|
| A61K 31/225 | (2006.01) | |
| C07C 229/00 | (2006.01) | |
| A61K 31/197 | (2006.01) | |
| A61K 31/221 | (2006.01) | |
| A61K 41/00 | (2006.01) | |
| A61K 45/06 | (2006.01) | |
| A61K 47/48 | (2006.01) | |
| A61N 5/06 | (2006.01) | |
| C07C 229/22 | (2006.01) | |

(52) U.S. Cl.
CPC .............. *A61N 5/062* (2013.01); *A61K 31/197* (2013.01); *A61K 31/221* (2013.01); *A61K 31/225* (2013.01); *A61K 41/0061* (2013.01); *A61K 45/06* (2013.01); *A61K 47/48023* (2013.01); *A61K 47/481* (2013.01); *A61K 2300/00* (2013.01); *C07C 229/22* (2013.01)

(58) Field of Classification Search
USPC ........................... 514/547; 560/170; 604/501
See application file for complete search history.

(56) References Cited

U.S. PATENT DOCUMENTS

| | | | | |
|---|---|---|---|---|
| 6,124,495 | A | 9/2000 | Neiss | |
| 7,799,782 | B2 * | 9/2010 | Munson et al. | 514/234.5 |
| 2002/0161045 | A1 | 10/2002 | Lan-Hargest | |
| 2006/0128618 | A1 | 6/2006 | Frank | |
| 2010/0184643 | A1 | 7/2010 | Goldfarb | |

OTHER PUBLICATIONS

Luk'yanets et al. CAS: 156: 29338, 2011.*
Berkovitch et al. CAS: 150: 15811, 2008.*
Berkovitch et al. CAS: 154: 559404, 2010.*
Amo et al., (2009) Mechanism of cell death by 5-aminolevulinic acid-based photodynamic action and its enhancement by ferrochelatase inhibitors in human histiocytic lymphoma cell line U937. Cell Biochem Funct 27(8): 503-515.
Aviram et al., (1997) Effect of the cytostatic butyric acid pro-drug, pivaloyloxymethyl butyrate, on the tumorigenicity of cancer cells. J Cancer Res Clin Oncol 123: 267-271.
Bao et al., (1999) Protein kinase B. (c-Akt), phosphotidylinositol 3-kinase and STAT5 are activated by EPO in HCD57 erythroid cells but are constitutively active in an EPO-independent, apoptosis resistant Subclone (HCD57-SREI cells). Blood 93(11): 3757-3773.
Berkovitch et al., (2008) Novel multifunctional acyloxyalkyl ester prodrugs of 5-aminolevulinic acid display improved anticancer activity independent and dependent on photoactivation. J Med Chem 51(23): 7356-7369.
Berkovitch et al., (2010) ALA-Butyrate prodrugs for Photo-Dynamic Therapy. Laser Florence 2009: a gallery through the laser medicine world. Book Series: AIP Conference Proceedings 1226: 45-51.
Berkovitch-Luria et al., (2012) A Multifunctional 5-Aminolevulinic acid Derivative Induces Erythroid Differentiation of K562 Human Erythroleukemic Cells. Eur J Pharm Sci 47(1): 206-214.
Berkovitch-Luria et al., (2012) Multifunctional 5-aminolevulinic acid Prodrugs Activating Diverse Cell-Death Pathways. Invest New Drugs 30(3): 1028-1038.

(Continued)

*Primary Examiner* — Rei-tsang Shiao
(74) *Attorney, Agent, or Firm* — Browdy and Neimark, PLLC

(57) ABSTRACT

The present invention provides drug conjugates comprising 5-aminolevulinic acid (ALA), an aldehyde and a carboxylic acid that may function as a histone deacetylase inhibitor (HDACI). These conjugates may serve as co-drugs which release a plurality of active species in vivo. The novel drug conjugates may be used, for the treatment or prevention of cancer in PDT-dependent and/or PDT-independent (nonPDT) treatments, as well as for cosmetic uses. In addition the present invention provides novel uses for both the novel and known compounds. According to some embodiments, the present invention provides drug conjugates (co-drugs) comprising (i) ALA, (ii) an aldehyde and (iii) a carboxylic acid that may function as a histone deacetylase inhibitor (HDACO for the treatment of anemia and/or for the induction of erythropoiesis.

21 Claims, 13 Drawing Sheets

(56) References Cited

OTHER PUBLICATIONS

Blank-Porat et al., (2007) The anticancer prodrugs of butyric acid AN-7 and AN-9, possess antiangiogenic properties. Cancer Lett 256(1): 39-48.
Bohlius et al., (2011) Twist and Shout: One Decade of Meta-Analyses of Erythropoiesis-Stimulating Agents in Cancer Patients. Acta Haematol 125: 55-67.
Chang et al., (1999) N-Acetylcysteine increases the biosynthesis of recombinant EPO in apoptotic Chinese hamster ovary cells. Free Radic Res 30: 85-91.
Daghman et al., (1999) Regulation of erythropoietin gene expression depends on two different oxygen-sensing mechanisms. Molec Genet Metabol 67(2): 113-117.
Encina and Sanz (2009) Photodynamic diagnosis (PDD) in non-muscle invasive bladder cancer. Actas Urol Esp 33(9): 965-975 (translated abstract).
Fallaux et al., (1996) The human clotting factor VIII cDNA contains an autonomously replicating sequence consensus-and matrix attachment region-like sequence that binds a nuclear factor, represses heterologous gene expression and mediates the transcriptional effects of sodium butyrate. Molec Cell Biol 16(8): 4264-4272.
Faris et al., (1999) The predictive power of baseline Hb for transfusion risk in surgery patients. Orthopedics 22(1): s135-s140.
Fibach (1993) Measurement of total and fetal hemoglobin in cultured human erythroid cells by a novel micromethod. Hemoglobin 17: 41-53.
Fibach et al., (1995) Hemin-induced acceleration of hemoglobin production in immature cultured erythroid cells: Preferential enhancement of fetal hemoglobin. Blood 85(10): 2967-2974.
Griggs and Bumberg (1998) Recombinant erythropoietin and blood transfusions in cancer chemotherapy-induced anemia. Anticancer Drugs 9(10): 925-932.
Grunberg-Etkovitz et al., (2006) Proteasomal degradation regulates expression of porphobilinogen deaminase (PBGD) mutants of acute intermittent porphyria. Biochim Biophys Acta 1762(9): 819-827.
Hermine et al., (1993) Hemin or butyrate increases constitutive erythropoietin formation by mouse erythroleukemia cell lines. Exp Hematol 21: 1207-11.
Hudgins et al., (1996) Transcriptional upregulation of •-globirby phenylbutyrate and analogous aromatic fatty acids. Biochem. Pharmacol 52(8): 1227-1233.
Inoue et al., (2007) Massive apoptotic cell death of human glioma cells via a mitochondrial pathway following 5-aminolevulinic acid-mediated photodynamic therapy. J Neurooncol 83(3): 223-231.
Jelkmann et al., (1997) Effects of antioxident vitamins on renal and hepatic EPO production. Kidney International 51 (2): 497-501.
Kawasaki et al., (1996) Control of Hemoglobin synthesis in erythroid differentiating K562 cells. I. Role of iron in erythroid cell heme synthesis. Arch Biochem Biophys 328(2): 289-294.
Kirito et al., (1998) A novel function of Stat1 and Stat3 proteins in erythropoietin-induced erythroid differentiation of a human leukemic cell line. Blood 92(2): 462-471.
Lopez et al., (2004) Photodynamic therapy of skin cancer: controlled drug delivery of 5-ALA and its esters. Adv Drug Deliver Rev 56(1): 77-94.
Malik and Lugaci (1987) Destruction of erythroleukaemic cells by photoactivation of endogenous porphyrins. Br J Cancer 56(5): 589-595.
Manner et al., (1998) Prospectus. Future trends in transfusion Clin Orthop 357: 101-15.
McCaffrey et al., (1997) Induction of gamma-globin by histone deacetylase inhibitors. Blood 90(5): 2075-2083.
Means (1999) Advances in the anemia of chronic disease. Int J Hematol 70(1): 7-11.
Neumcke et al., (1999) Effect of pro- and antioxidative compound on renal production of erythropoietin. Endocrinology 140(2): 641-645.
Nudelman et al., (1992) Novel anticancer prodrugs of butyric acid. 2. J Med Chem 35(4): 687-694.
Nudelman et al., (2005) The role of intracellularly released formaldehyde and butyric acid in the anticancer activity of acyloxyalkyl esters. J Med Chem 48(4): 1042-1054.
Prince et al., (2009) Clinical Studies of Histone Deacetylase Inhibitors. Clin Cancer Res 15(12): 3958-3969.
Qvist et al., (1999) Recombinant human EPO and Hb concentration at operation and during the postoperative period: reduced need for blood transfusion in patients undergoing colorectal surgery—prospective double-blind placebo-controlled study. World J Surg 23(1): 30-35.
Rabizadeh et al., (1990) Effects of pivaloyloxymethyl butyrate on leukemic cells differentiation and proliferation and of mononuclear cells lymphokine(s) secretion. Blood 76 suppl. 1: 113a/444.
Rephaeli et al,. (1995) A novel butyric acid derivative stimulate fetal Hb expression. In: "Sickle cell disease and thalassaemias: New Trends in Therapy" Eds. Y. Beusard, B. Lubin, J. Ross. Colloque INSETN John Libbey Eurotext Ltd. 234: 215-216.
Rephaeli et al., (1991) Derivatives of butyric acid as potential antineoplastic agents. Int J Cancer 49(2): 66-72.
Rephaeli et al., (2000) Prodrugs of butyric acid from bench to bedside: synthetic design, mechanisms of action and clinical applications. Drug Developt Res 50(3-4): 379-390.
Rephaeli et al., (2006) The selectivity and anti-metastatic activity of oral bioavailable butyric acid prodrugs. Invest New Drugs 24(5): 383-392.
Rosato and Grant (2004) Histone deacetylase inhibitors in clinical development. Expert Opin Investig Drugs 13: 21-38.
Taher et al., (2009) Effects of divalproex sodium on Hb level. Blood Cells Mol Dis 43(1): 49-52.
Tarasenko et al., (2008) Histone deacetylase inhibitors: the anticancer, antimetastatic and antiangiogenic activities of AN-7 are superior to those of the clinically tested AN-9 (Pivanex). Clin Exp Metastasis 25(7): 703-716.
Trovarelli et al., (1998) Transfusion-free surgery is a treatment plan for all patients. AORN J 68(5): 773-778, 780-784.
Weinberg et al., (2005) Butyrate increases the efficiency of translation of gamma-globin mRNA. Blood 105 (4):1807-1809.
Wolffe (1997) Sinful repression. Nature 387: 16-17.
Xu et al., (2007) Histone deacetylase inhibitors: molecular mechanisms of action. Oncogene 26(37): 5541-5552.

* cited by examiner

5-AMINOLEVULINIC ACID DERIVATIVES, METHODS FOR THEIR PREPARATION AND USES THEREOF

FIELD OF THE INVENTION

The present invention relates to drug conjugates comprising 5-aminolevulinic acid (5-ALA), an aldehyde and a carboxylic acid (e.g., histone deacetylase inhibitor (HDACI)), compositions comprising them and uses thereof for treatment of cancer and anemia and for inducing erythropoiesis.

BACKGROUND OF THE INVENTION

Photodynamic therapy (PDT) is a promising type of non-invasive therapy, and favorable results of PDT have been reported in glioma patients [1]. In general, PDT involves at least the components of a photosensitizer and irradiating light (at a wavelength appropriate for the photosensitizer). The light causes the photosensitizer to damage and kill cells and tissues exposed to the irradiated light. Aminolevulinic acid (ALA)-PDT therapy is based on the administration of aminolevulinic acid (ALA), the natural precursor for protoporphyrin IX (PpIX) biosynthesis, which is a potent natural photosensitizer. Irradiation of ALA treated cancer cells in the presence of oxygen results in generation of singlet oxygen that is toxic to the tumor [2]. ALA-PDT is the most used phototherapy application for skin cancers such as basal cell carcinomas and in addition, ALA based photo-diagnosis is used for intraoperative dissection of gliomas and bladder tumors [3]. A main disadvantage of ALA-PDT is the hydrophilic nature of ALA, which limits its ability to penetrate deeper into tissue layers. One solution to improve the poor penetrability of ALA is to increase its lipophilicity using ALA esters such as methyl-ALA and hexyl-ALA [4].

It has been shown that ALA acyloxyalkyl ester prodrugs are hydrolyzed into ALA which induces PpIX synthesis [5]. The advantage of these ALA-prodrugs stems from their ability to induce cancer cells death by both PDT and non-PDT mechanisms at doses lower than ALA.

Pharmacological inhibition of histone deacetylase (HDAC) activity by small organic molecules (HDACIs) could provide therapeutic benefit to a variety of diseases and disorders [6]. Histone deacetylase inhibitory prodrugs which are small molecular weight fatty acids, that upon intracellular hydrolytic degradation release acids and aldehydes have been described [7-9]. These compounds have been shown to modulate gene expression, induce histone hyperacetylation, differentiation, and apoptosis of cancer cells in vitro, ex-vivo and in vivo [10-12].

Anemia is a common, and sometimes the major, clinical symptom of a wide variety of pathological conditions [13]. Its severity is determined by two parameters: the number of red blood cells (RBC) and their hemoglobin (Hb) content. Erythropoietin (EPO) is the major stimulating hormone of red blood cell formation (erythropoiesis). It is produced, principally, in the kidney, and its levels are controlled by tissue oxygen tension. In bone marrow, it promotes the survival, proliferation and maturation of the erythroid progenitors and precursor cells thus leading to the elevation of red cell mass and Hb level. Several types of anemia can be ameliorated by EPO. It has been used primarily in cases of anemia due to EPO-insufficiency associated with chronic renal failure, and also for anemia due to different cases. EPO has also been introduced as a preemptive/prophylactic treatment for patients undergoing elective surgery, to avoid heterologous blood transfusion. Although the latter procedure is safe in most cases, it is not without risk due to blood-borne pathogens, immunomodulating factors and severe allergic reactions. In an alternative approach, autologous blood is used for transfusions; patients are phlebotomized prior to surgery, RBC harvested and stored, and then used during or following the operation. Nevertheless, treatment with EPO, the costs of which are high, increases the yield of the RBC harvested and ameliorates the transient phase of mild anemia that might follow. Moreover, in placebo-controlled studies, administration of EPO prior to surgery increased Hb level at and after surgery and significantly lowered the need for blood transfusions [14]. Although meta analyses on the effect of EPO on cancer patients indicated increase in life quality benefit, it also showed increased risks for thromboembolic and cardiovascular events.

Thus, there is a need in the art for improved methods for treatment of anemia, that are less toxic and less expensive. In particular, it would be advantageous to have drugs that can replace EPO or reduce the dose of EPO required for treating anemia.

SUMMARY OF THE INVENTION

The present invention provides drug conjugates comprising 5-aminolevulinic acid (ALA), an aldehyde and a carboxylic acid that may function as a historic deacetylase inhibitor (HDACI). These conjugates may serve as co-drugs which release a plurality of active species in vivo. The novel drug conjugates may be used, for the treatment or prevention of cancer in PDT-dependent and/or PDT-independent (non-PDT) treatments, as well as for cosmetic uses.

In addition the present invention provides novel uses for both the novel and known compounds. According to some embodiments, the present invention provides drug conjugates (co-drugs) comprising (i) ALA, (ii) an aldehyde and (iii) a carboxylic acid that may function as a histone deacetylase inhibitor (HDACI) for the treatment of anemia and/or for the induction of erythropoiesis.

According to some embodiments, there are provided compounds represented by the structure of formula (I):

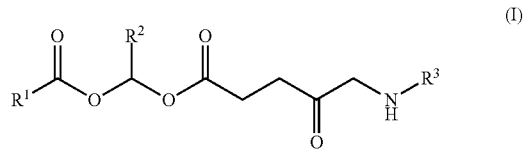

wherein
R$^1$ is
(a) a $C_1$-$C_{20}$ straight, branched, saturated or unsaturated or cyclic alkyl, wherein said alkyl may be unsubstituted or substituted with a phenyl, halogen, or oxygen;
(b) —$CH_2CH_2$—CO—$CH_2$—NH—R$^3$; or
(c) —CH(NHCOCH$_3$)CH$_2$—SH;
R$^2$ is H or a $C_1$-$C_{20}$ straight, branched, saturated or unsaturated, or cyclic alkyl, wherein said alkyl may be unsubstituted or substituted with a phenyl, halogen, or oxygen; and
R$^3$ is H or a nitrogen protecting group;
or a pharmaceutically acceptable salt thereof;
with the proviso that when R$^1$COO is derived from pivalic, butyric or valproic acid, R$^2$ is not H or CH$_3$;

including salts, polymorphs, optical isomers, geometrical isomers, enantiomers, diastereomers, and mixtures thereof.

The group $R^1C(=O)—O—$ is derived from a carboxylic acid of formula $R^1C(=O)OH$, wherein $R^1$ is as defined above. In some embodiments, $R^1C(=O)O—$ is derived from a carboxylic acid selected from the group consisting of pivalic, butyric, valeric, hexanoic, 4-phenylbutyric, 4-phenylacetic, heptanoic, octanoic, decanoic, and retinoic acid. Currently preferred carboxylic acids are butyric, octanoic, decanoic, valeric or retinoic acid, and particularly preferred are butyric acid or octanoic acid. Each possibility represents a separate embodiment of the present invention.

According to some embodiments, $R^1$ is a $C_1$-$C_{10}$ straight, branched, saturated or unsaturated or cyclic alkyl, wherein said alkyl may be unsubstituted or substituted with a phenyl, halogen, or oxygen. In further embodiments, $R^1$ may be a $C_3$-$C_{10}$ straight, branched, saturated or unsaturated or cyclic alkyl, wherein said alkyl may be unsubstituted or substituted with a phenyl, halogen, or oxygen. In further embodiments, $R^1$ may be a $C_{10}$-$C_{20}$ straight, branched, saturated or unsaturated or cyclic alkyl, wherein said alkyl may be unsubstituted or substituted with a phenyl, halogen, or oxygen. In some embodiments, $R^1$ is selected from the group consisting of methyl, ethyl, propyl, butyl, pentyl, hexyl, heptyl, octyl, nonanyl and decyl, with propyl and heptyl being currently preferred.

The group $R^2—(CH)—O—$ is derived from an aldehyde of formula $R^2C(=O)H$, wherein $R^2$ is as defined above. According to some embodiments, the aldehyde is formaldehyde (in which case $R^2$ is H). According to other embodiments, the aldehyde is acetaldehyde (in which case $R^2$ is $CH_3$). According to other embodiments, the aldehyde is propionaldehyde (in which case $R^2$ is $CH_2CH_3$). According to other embodiments, the aldehyde is butyrladehyde (in which case $R^2$ is $CH_2CH_2CH_3$). In further embodiments, $R^2$ is a C4-C10 straight, branched, saturated or unsaturated or cyclic alkyl, wherein said alkyl may be unsubstituted or substituted with a phenyl, halogen, or oxygen. Each possibility represents a separate embodiment of the present invention.

According to some embodiments, $R^3$ is H. In further embodiments, $R^3$ is a nitrogen protecting group selected from Boc and Cbz.

Non-limiting examples of compounds of formula (I) according to the present invention are compounds of formula (A), (B) and (C):

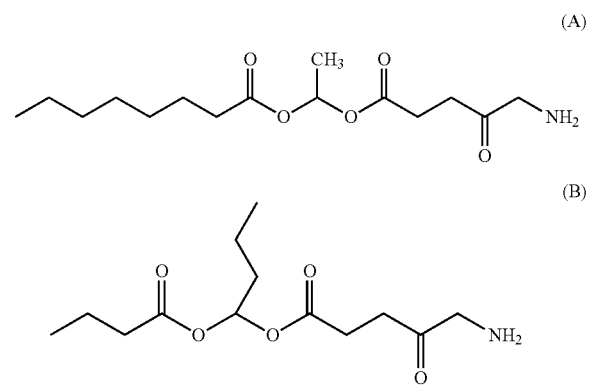

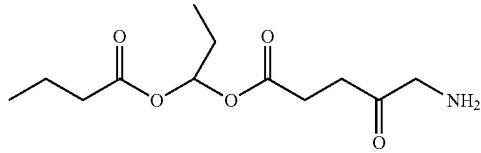

Compounds A-C are represented by the following chemical names:
1-(Octanoyloxy)ethyl-5-amino-4-oxopentanoate (A);
1-(Butyryloxy)butyl-5-amino-4-oxopentanoate (B);
1-(Butyryloxy)propionyl-5-amino-4-oxopentanoate hydrochloride (C).

In some embodiments, the compounds of formula (A) to (C) are provided in the form of pharmaceutically acceptable salts, preferably the hydrochloride (HCl) salts.

In some embodiments, the compound of formula (I) is in the form of an acid addition salt. The salt may be derived from a pharmaceutically acceptable acid selected from the group consisting of hydrochloric, hydrobromic, sulfuric, methane sulfonic, benzene sulfonic, naphthyl sulfonic, acetic, tartaric, maleic and malic acids. Currently preferred acid addition salts are hydrochloric acid (HCl) salts.

According to additional embodiments, there is provided a pharmaceutical composition comprising a compound of formula (I), and a pharmaceutically acceptable carrier or excipient. In some embodiments, the pharmaceutical composition is in a form suitable for oral administration, intravenous administration by injection, topical administration, dermatological administration, administration by inhalation, or administration via a suppository.

In additional embodiments, there is provided a pharmaceutical composition comprising a compound of formula (I) that is in a form suitable for topical or dermatological administration, and the composition further comprises a topically or dermatologically acceptable carrier or excipient.

Each compound of the present invention may be formulated in such a pharmaceutical composition, with each possibility representing a separate embodiment of the present invention. In a currently preferred embodiment, the pharmaceutical composition of the present invention comprises a compound of formula (I) or (I-a) wherein $R^1CO°$ is derived from retinoic acid, and further comprises a topically or dermatologically acceptable carrier or excipient.

According to some embodiments, the compounds of formula (I) are co-drugs, that may be hydrolyzed in-vivo, to produce one or more active compounds that may exert a biological effect. In some embodiments, the compounds of formula (I) may be hydrolyzed to 5-ALA, a carboxylic acid and an aldehyde. In some embodiments, the carboxylic acid may be an inhibitor of histone deacetylase (that is, the carboxylic acid may be an HDACI).

According to some embodiments, the present invention relies at least in part on the finding that derivatives of 5-ALA and HDACI (which may be derived from co-drug compounds represented by Formula (I) upon in-vivo hydrolysis), improve the neoplastic activities of dependent photodynamic therapy (PDT) and independent photodynamic therapy (non-PDT) and specifically affect cancer cells with a substantially lower effect on normal cells.

According to some embodiments, the acyloxymethyl ester co-drug(s) of Formula (I) are highly active in PDT-independent (non-PDT) anti cancer treatment. In some embodiments, the acyloxyalkyl co-drugs of formula (I) elicit high photodynamic-dependent antineoplastic activity. In some embodiments, co-drugs represented by compounds of formula (I) are hydrolyzed in-vivo to yield 5-ALA and a carboxylic acid, wherein the carboxylic acid may be an HDACI. In some embodiments, the HDACI is an octanoic acid.

According to some embodiments, there is thus provided a method for the treatment or prevention of cancer, comprising the step of administering to a subject in need thereof the compound of formula (I) or pharmaceutical composition comprising the same.

According to some embodiments, the treatment or prevention of cancer is selected from photodynamic therapy (PDT), non-photodynamic therapy (non-PDT), or a combination thereof. In some embodiments, when $R^2$ is H, the cancer treatment comprises non-photodynamic therapy (non-PDT). In some embodiments, when $R^2$ is a $C_1$-$C_{20}$ straight, branched, saturated or unsaturated, or cyclic alkyl, and the cancer treatment comprises photodynamic therapy (PDT).

According to further embodiments, there is provided a method for the treatment or prevention of cancer, comprising the step of administering to a subject in need thereof a therapeutically effective amount of octanoic acid or a therapeutically acceptable salt thereof.

According to some embodiments, there are provided compounds of formula (I-a), for use in the treatment or prevention of anemia, wherein the compound(s) of formula (I-a) are represented by the following structure:

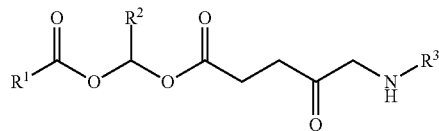

(I-a)

wherein
$R^1$ is
  (a) a $C_1$-$C_{20}$ straight, branched, saturated or unsaturated or cyclic alkyl, wherein said alkyl may be unsubstituted or substituted with a phenyl, halogen, or oxygen;
  (b) —$CH_2CH_2$—CO—$CH_2$—NH—$R^3$; or
  (c) —$CH(NHCOCH_3)CH_2$—SH;
$R^2$ is a $C_1$-$C_{20}$ straight, branched, saturated or unsaturated, or cyclic alkyl, wherein said alkyl may be unsubstituted or substituted with a phenyl, halogen, or oxygen; and
$R^3$ is H or a nitrogen protecting group;
or a pharmaceutically acceptable salt thereof;
including salts, polymorphs, optical isomers, geometrical isomers, enantiomers, diastereomers, and mixtures thereof.

The group $R^1C(=O)$—O— is derived from a carboxylic acid of formula $R^1C(=O)OH$, wherein $R^1$ is as defined above. In some embodiments, $R^1C(=O)O$— is derived from a carboxylic acid selected from the group consisting of pivalic, butyric, valeric, hexanoic, 4-phenylbutyric 4-phenylacetic, heptanoic, octanoic, decanoic, and retinoic acid. Currently preferred carboxylic acids are butyric, octanoic, decanoic, valeric or retinoic acid, and aparticularly preferred are butyric acid or octanoic acid. Each possibility represents a separate embodiment of the present invention.

According to some embodiments, $R^1$ is a $C_1$-$C_{10}$ straight, branched, saturated or unsaturated or cyclic alkyl, wherein said alkyl may be unsubstituted or substituted with a phenyl, halogen, or oxygen. In further embodiments, $R^1$ may be a $C_5$-$C_{10}$ straight, branched, saturated or unsaturated or cyclic alkyl, wherein said alkyl may be unsubstituted or substituted with a phenyl, halogen, or oxygen. In further embodiments, $R^1$ may be a $C_{10}$-$C_{20}$ straight, branched, saturated or unsaturated or cyclic alkyl, wherein said alkyl may be unsubstituted or substituted with a phenyl, halogen, or oxygen. In some embodiments, $R^1$ is selected from the group consisting of methyl, ethyl, propyl, butyl, pentyl, hexyl, heptyl, octyl, nonanyl and decyl.

The group $R^2$—(CH)—O— is derived from an aldehyde of formula $R^2C(=O)H$, wherein $R^2$ is as defined above. According to some embodiments, the aldehyde is formaldehyde (in which case $R^2$ is H). According to other embodiments, the aldehyde is acetaldehyde (in which case $R^2$ is $CH_3$). According to other embodiments, the aldehyde is propionaldehyde (in which case $R^2$ is $CH_2CH_3$). According to other embodiments, the aldehyde is butyrladehyde (in which case $R^2$ is $CH_2CH_2CH_3$). In further embodiments, $R^2$ is a $C_4$-$C_{10}$ straight, branched, saturated or unsaturated or cyclic alkyl, wherein said alkyl may be unsubstituted or substituted with a phenyl, halogen, or oxygen. Each possibility represents a separate embodiment of the present invention.

According to some embodiments, $R^3$ is H. In further embodiments, $R^3$ is a nitrogen protecting group selected from Boc and Cbz.

Non-limiting examples of compounds of formula (I-a) according to the present invention are compounds of formula (A), (B) and (C) as shown above, and further compounds of formula (D) to (G), as defined hereinbelow:

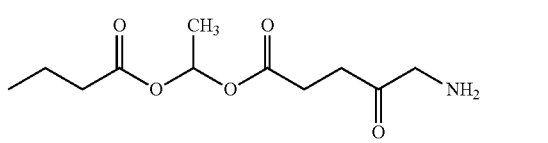

(D)

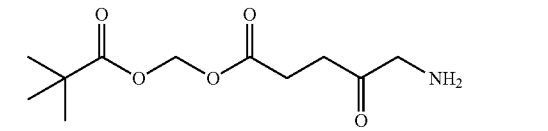

(E)

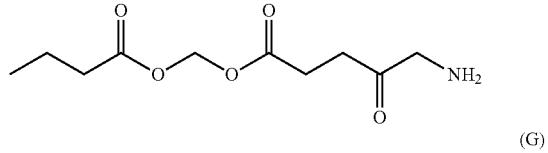

(F)

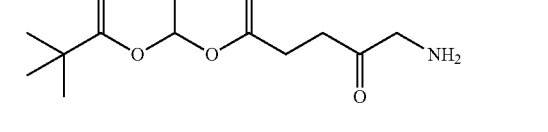

(G)

Compounds D-G are represented by the following chemical names:
  1-(butyryloxy)ethyl 5-amino-4-oxopentanoate (D);
  (pivaloyloxy)methyl 5-amino-4-oxopentanoate (E);
  (butyryloxy)methyl 5-amino-4-oxopentanoate (F);
  1-(pivaloyloxy)ethyl 5-amino-4-oxopentanoate (G).

In some embodiments, the compounds of formula (D) to (G) are provided in the form of pharmaceutically acceptable salts, preferably the hydrochloride (HCl) salts.

In some embodiments, the compound of formula (I-a) is in the form of an acid addition salt. The salt may be derived from a pharmaceutically acceptable acid selected from the group consisting of hydrochloric, hydrobromic, sulfuric, methane sulfonic, benzene sulfonic, naphthyl sulfonic, acetic, tartaric, maleic and malic acids. Currently preferred acid addition salts are hydrochloric acid (HCl) salts.

According to further embodiments, there is provided a method for inducing erythropoiesis, comprising the step of administering to a subject in need thereof a compound represented by the structure of formula (I-a), or a pharmaceutical composition comprising such compound.

According to some embodiments, there are provided compounds of formula (I-a), for use in the treatment or prevention of anemia and/or for induction of erythropoiesis.

According to some embodiments, the compounds represented by formula (I-a) are co-drugs, that may be hydrolyzed in-vivo, to produce one or more active compounds that may exert a biological effect. In some embodiments, the compounds of formula (I-a) may be hydrolyzed to 5-ALA, a carboxylic acid and an aldehyde. In some embodiments, the carboxylic acid may be an inhibitor of histone deacetylase (that is, the carboxylic acid may be an HDACI). In some embodiments, the HDACI is an octanoic acid. In some embodiments, the HDACI is Butyric acid.

According to further embodiments, the compounds represented by formula (I-a) may be used to induce differentiation of erythrocytes and to induce erythropoiesis.

According to some embodiments, there are further provided pharmaceutical compositions comprising a therapeutically effective amount of at least one compound represented by the structure of formula (I-a). Such pharmaceutical compositions may be used, in some embodiments, for the treatment or prevention of anemia in a subject. In some embodiments, such pharmaceutical compositions may be used for induction of erythropoiesis in a subject.

According to further embodiments, there is provided a method for the treatment or prevention of anemia, comprising the step of administering to a subject in need thereof a combination comprising an HDAC-inhibitor and 5-aminolevulinic acid (5-ALA) or an ester thereof, wherein the ester is a methyl or a hexyl ester.

In some embodiments, the pharmaceutical composition is in a form suitable for oral administration, intravenous administration by injection, topical administration, dermatological administration, administration by inhalation, or administration via a suppository.

In additional embodiments, there is provided a pharmaceutical composition comprising a compound of formula (I-a) that is in a form suitable for topical or dermatological administration, and the composition further comprises a topically or dermatologically acceptable carrier or excipient.

In addition to the aspects and embodiments described above, further aspects and embodiments will become apparent by reference to the figures and by study of the following detailed description.

BRIEF DESCRIPTION OF THE FIGURES

Some embodiments are illustrated in referenced figures. Dimensions of components and features shown in the figures are generally chosen for convenience and clarity of presentation and are not necessarily shown to scale. The figures are listed below.

FIG. 2A—shows a representative histogram depicting flow cytometry analysis of PpIX expression. FIG. 2B shows pictures of cells expressing PpIX;

FIG. 3A shows a bar graph of the relative activity of PGBD compared to control. FIG. 3B shows a western blot analysis of the expression of PBGD in the cells. FIG. 3C shows a bar graph of quantitative RT-PCT analysis of the expression of PBGD mRNA in the cells, in response to various treatments. FIG. 3D shows a western blot analysis of the expression of Ferrochelatase in the cells. FIG. 3E shows a FACS analysis of the expression of Ferrochelatase in the cells;

FIG. 4A shows a bar graph of the fold increase in total heme content. FIG. 4B shows a bar graph of the fold increase in total heme content in response to treatment with various compounds of formula (I-a) (D, 1-(butyryloxy)ethyl 5-amino-4-oxopentanoate (AlaAcBu), compound D, above; C, 1-(Butyryloxy)propionyl-5-amino-4-oxopentanoate hydrochloride, compound C, above; B, 1-(Butyryloxy)butyl-5-amino-4-oxopentanoate Hydrochloride, compound B, above). FIG. 4C shows a bar graph of the fold increase in mRNA expression of α-globin under various treatments. FIG. 4D show a Western blot analysis of the expression levels of α-globin. FIG. 4E show a bar graph of the expression levels of α-globin protein;

FIG. 5A shows a bar graph of the relative expression of glycophorin A. FIG. 5B shows a representative histogram depicting flow cytometry analysis of glycophorin A expression;

FIG. 6A shows a bar graph illustrating the mitochondria activity (% of control) under various treatments as measured by MTT assay. FIG. 6B shows FACS analysis of the cells under different experimental conditions;

FIG. 8A is a scheme of the experiment protocol, showing the treatment regime of the tested compounds of the tested groups: Group I (treated with Doxorubicin alone) and Group II (treated with Doxorubicin and a compound of Formula (I-a). FIG. 8B is a bar graph of the amount of hemoglobin (mg/mL) in blood retrieved from Balb-c mice treated with doxorubicin (DOX) or doxorubicin in combination with a compound of formula (I-a) ((in this example, AlaAcBu), (marked in the figure as DOX+1−a)).

FIG. 9A shows the effect of octanoic acid on the activity of HDAC in glioblastoma cell line U251. FIG. 9B shows the effect of compound of formula (I-a) on the activity of HDAC in glioblastoma cell line U251.

DETAILED DESCRIPTION OF THE INVENTION

Definitions

Figure 1:
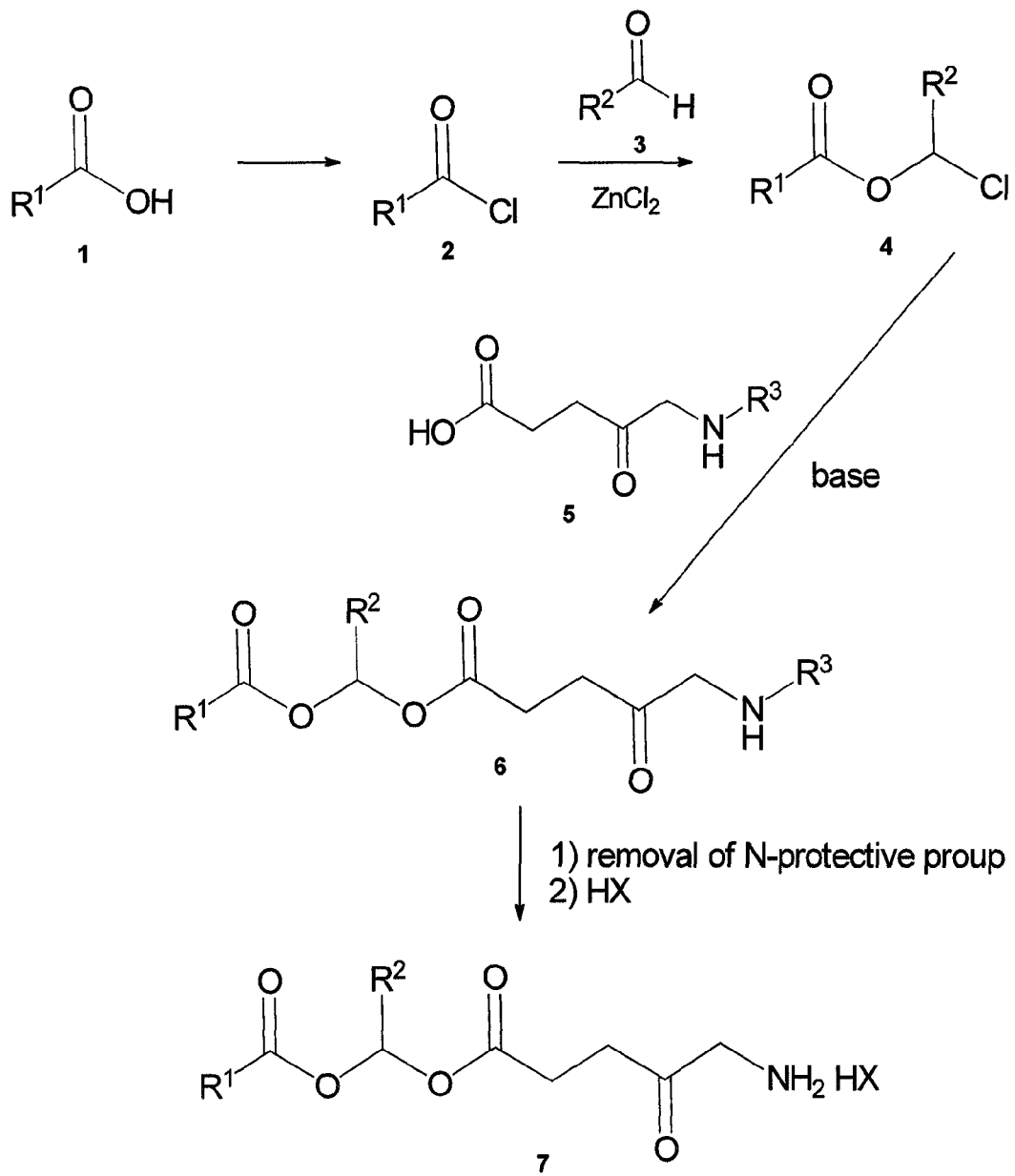
FIG. 1 shows in schematic form a process for the synthesis of compounds I and (I-a), according to some embodiments.

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

An "alkyl" group refers to any saturated or unsaturated aliphatic hydrocarbon, including straight-chain, branched-chain and cyclic alkyl groups. It is understood that an "unsaturated alkyl" refers to an "alkenyl" or "alkynyl" group, as defined herein, and that a "cyclic alkyl group" refers to a cycloalkyl group as defined herein. In one embodiment, the alkyl group has 1-20 carbons designated here as $C_1$-$C_{20}$-alkyl. In another embodiment, the alkyl group has 1-10 carbons designated here as $C_1$-$C_{10}$-alkyl. In another embodiment, the alkyl group has 1-5 carbons designated here as $C_1$-$C_5$-alkyl. The alkyl group may be unsubstituted or substituted by one or more groups selected from halogen, hydroxy, alkoxy, aryloxy, alkylaryloxy, heteroaryloxy, oxo, cycloalkyl, phenyl, heteroaryl, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, $C_1$ to $C_{10}$ alkylthio arylthio, or $C_1$ to $C_{10}$ alkylsulfonyl groups. Any substituent can be unsubstituted or further substituted with any one of these aforementioned substituents.

An "alkenyl" group refers to an aliphatic hydrocarbon group containing at least one carbon-carbon double bond including straight-chain and branched-chain alkenyl groups. In one embodiment, the alkenyl group has 2-8 carbon atoms designated here as $C_2$-$C_8$-alkenyl. In another embodiment, the alkenyl group has 2-6 carbon atoms in the chain designated here as $C_2$-$C_6$-alkenyl. Exemplary alkenyl groups include ethenyl, propenyl, n-butenyl, i-butenyl, 3-methylbut-2-enyl, n-pentenyl, heptenyl, octenyl, cyclohexyl-butenyl and decenyl. The alkenyl group can be unsubstituted or substituted through available carbon atoms with one or more groups defined hereinabove for alkyl.

An "alkynyl" group refers to an aliphatic hydrocarbon group containing at least one carbon-carbon triple bond including straight-chain and branched-chain. In one embodiment, the alkynyl group has 2-8 carbon atoms in the chain designated here as $C_2$-$C_8$-alkynyl. In another embodiment, the alkynyl group has 2-6 carbon atoms in the chain designated here as $C_2$-$C_6$-alkynyl. Exemplary alkynyl groups include ethynyl, propynyl, n-butynyl, 2-butynyl, 3-methylbutynyl, n-pentynyl, heptynyl, octynyl and decynyl. The alkynyl group can be unsubstituted or substituted through available carbon atoms with one or more groups defined hereinabove for alkyl.

A "cycloalkyl" group refers to any saturated or unsaturated (e.g., cycloalkenyl, cycloalkynyl) monocyclic or polycyclic group. In some emobdiments, the cycloalkyl group has 3-20 carbon atoms designated here as $C_3$-$C_{20}$-cycloalkyl. The cycloalkyl group may be monocyclic, fused bicyclic or tricyclic, etc. Non-limiting examples of cycloalkyl groups are cyclopropyl, cyclobutyl, cyclopentyl, cyclohexyl or cycloheptyl. Non-limiting examples of cycloalkenyl groups include cyclopentenyl, cyclohexenyl and the like. The cycloalkyl group can be unsubstituted or substituted with any one or more of the substituents defined above for alkyl.

As used herein, the term "nitrogen protecting group" (P) refers to a group which may be attached to a nitrogen atom to protect said nitrogen atom from participating in a reaction and which may be readily removed following the reaction. The nitrogen protecting group can be an acid labile protecting group, a base labile protecting group, or a protecting group that is removable under neutral conditions. Non-limiting examples of nitrogen-protecting groups are silyl protecting groups [$Si(R)_3$ wherein R is alkyl, aryl, aralkyl, and the like], acyl groups such as acetyl ($COCH_3$), benzoyl, 2-bromoacetyl, 4-bromobenzoyl, tert-butylacetyl, carboxaldehyde, 2-chloroacetyl, 4-chlorobenzoyl, α-chlorobutyryl, 4-nitrobenzoyl, o-nitrophenoxyacetyl, phthalyl, pivaloyl, propionyl, trichloroacetyl, and trifluoroacetyl; amide groups such as acetamide and the like; sulfonyl groups such as benzenesulfonyl, and p-toluenesulfonyl; carbamate groups of the formula —C(O)O—R wherein R is for example methyl, ethyl, t-butyl, benzyl, phenylethyl, $CH_2$=$CH$—$CH_2$, such as benzyloxycarbonyl (Cbz), tert-butyloxycarbonyl (Boc), p-chlorobenzyloxycarbonyl, p-methoxybenzyloxycarbonyl, and the like. Other suitable nitrogen protecting group include, but are not limited to: benzyl, formyl, phenylsulfonyl, (Fmoc), p-nitrobenzenesulfoethoxycarbonyl propargyloxycarbonyl, picolinyl, prenyl, o-nitrobenzyloxy methyl, 4-methyoxyphenoxymethyl, guaiacolmethyl, siloxymethyl, such as triisopropylsiloxymethyl, 2-cyanoethyoxymethyl, 2-quinolinylmethyl, dichloroacetyl, trichloroacetyl and 2-[4-nitrophenyl]ethylsulfonate, as well as benzyl, p-methoxy benzyl and trityl. Each possibility represents a separate embodiment of the invention. A currently preferred protecting group is Boc. Another currently preferred protecting group is Cbz.

Other examples of nitrogen-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3, each of which is incorporated herein by reference.

All references cited herein are hereby incorporated by reference in their entirety, as if fully set forth herein.

As used herein, the term "salt" encompasses both basic and acid addition salts, including but not limited to carboxylate salts or salts with amine nitrogens, and include salts formed with the organic and inorganic anions and cations discussed below. Further encompassed by the term are salts formed by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, naphthylsulfonic, sorbic, picric, benzoic, cinnamic, and the like.

All stereoisomers of the compounds of the present invention are contemplated, either in admixture or in pure or substantially pure form. These compounds can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, l,L or d,l, D,L. In addition, several of the compounds of the present invention may contain one or more double bonds. The present invention intends to encompass all structural and geometrical isomers including cis, trans, E and Z isomers and optical isomers, independently at each occurrence. The thioamides of the present invention occur in two isomeric forms known as atropisomers, due to hindered rotation around the thioamide bond. These isomers can interconvert in solution and ratios may vary at different conditions including temperature, pH, solvent, concentration, and the like.

The term "treating" as used herein refers to abrogating, inhibiting, slowing or reversing the progression of a disease or condition, ameliorating clinical symptoms of a disease or condition or preventing the appearance of clinical symptoms of a disease or condition. The term "preventing" is defined herein as barring a subject from acquiring a disorder or disease or condition.

The term "treatment of cancer" is directed to include at least one of the following: a decrease in the rate of growth of the cancer (i.e. the cancer still grows but at a slower rate); cessation of growth of the cancerous growth, i.e., stasis of the tumor growth, and, in preferred cases, the tumor diminishes or is reduced in size. The term also includes reduction in the number of metastases, reduction in the number of new metastases formed, slowing of the progression of cancer from one stage to the other and a decrease in the angiogenesis induced by the cancer. In most preferred cases, the tumor is totally eliminated. Additionally included in this term is lengthening of the survival period of the subject undergoing treatment, lengthening the time of diseases progression, tumor regression, and the like.

The term "therapeutically effective amount" refers to the amount of a compound being administered which provides a therapeutic effect for a given condition and administration regimen, specifically an amount which relieves to some extent one or more of the symptoms of the disorder being treated.

As used herein, the term "introducing" refers to the transfer of molecules/compounds, into a target site, that may include, for example, a cell, a tissue, an organ, and the like. The molecules can be "introduced" into the target cell(s) by any means known to those of skill in the art. Introduction into the cells may be passive (for example, by incubating the cells with the compounds). Introduction into the cells may take use of various agents that are able to mediate/facilitate/allow the entrance of the compound into the cell. The cells may be selected from isolated cells, tissue cultured cells, cell lines, cells present within an organism body, and the like.

As referred to herein, the term "HDAC" is directed to histone deacetylase or lysine deacetylase. Histone deacetylase(s) or lysine deacetylase are a class of enzymes that remove acetyl group(s) from an e-N-acetyl lysine amino acid on a histone or other proteins. Its action is opposite to that of histone acetyltransferase.

As referred to herein, the term "HDACI" is directed to histone deacetylase inhibitor(s). HDACI are compounds which are able to inhibit the activity of histone deacetylase or lysine deacetylase.

As referred to herein, the terms "ALA" and "5-ALA" may interchangeably be used and are directed to 5-aminolevulinic acid.

As referred to herein, the terms "co-drug(s)" and "drug conjugate(s)" may interchangeably be used. The terms are directed to a single molecule compound, which upon in-vivo processing (for example, by hydrolysis) may yield two or more separate compounds/reagents, each may be active in vivo. The processing of the co-drug may be performed in vivo, for example, within cell, within a tissue, within an organ, and the like. The co-drug may be inactive when administered, but may be converted in vivo to two or more active compound(s)/components. In some embodiments, the co-drug may be formulated to a pharmaceutical composition.

As referred to herein, the term "mixture" is directed to a mixture of two or more separate compounds/reagents that may be present in the same composition and may be administered in combination (simultaneously or sequentially).

According to some embodiments, there are provided compounds represented by the structure of formula (I):

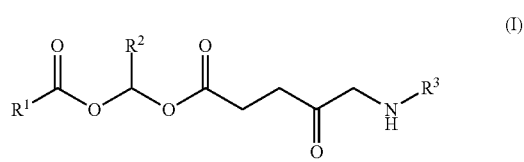

wherein
$R^1$ is
(a) a $C_1$-$C_{20}$ straight, branched, saturated or unsaturated or cyclic alkyl, wherein said alkyl may be unsubstituted or substituted with a phenyl, halogen, or oxygen;
(b) —$CH_2CH_2$—CO—$CH_2$—NH—$R^3$; or
(c) —CH(NHCOCH$_3$)CH$_2$—SH;
$R^2$ is H or a $C_1$-$C_{20}$ straight, branched, saturated or unsaturated, or cyclic alkyl, wherein said alkyl may be unsubstituted or substituted with a phenyl, halogen, or oxygen; and
$R^3$ is H or a nitrogen protecting group;
or a pharmaceutically acceptable salt thereof;
with the proviso that when $R^1$COO is derived from pivalic, butyric or valproic,
$R^2$ is not H or $CH_3$;
including salts, polymorphs, optical isomers, geometrical isomers, enantiomers, diastereomers, and mixtures thereof.

In some embodiments, the group $R^1C(=O)$—O— is derived from a carboxylic acid of formula $R^1C(=O)OH$, wherein $R^1$ is as defined above. In some embodiments, $R^1C(=O)O$— is derived from a carboxylic acid selected from the group consisting of pivalic, butyric, valeric, hexanoic, 4-phenylbutyric, 4-phenylacetic, heptanoic, octanoic, decanoic, and retinoic acid. Currently preferred carboxylic acids are butyric, octanoic, decanoic, valeric or retinoic acid, and aparticularly preferred are butyric acid or octanoic acid. Each possibility represents a separate embodiment of the present invention.

According to some embodiments, $R^1$ is a $C_1$-$C_{20}$ straight or branched chain alkyl, a $C_2$-$C_{20}$ alkenyl, a $C_2$-$C_{20}$ alkynyl or a $C_3$-$C_{20}$ cycloalkyl, wherein said alkyl, alkenyl, alkynyl or cycloalkyl may be unsubstituted or substituted with a phenyl, halogen, or oxygen.

According to some embodiments, $R^1$ is a $C_1$-$C_{10}$ straight, branched, saturated or unsaturated or cyclic alkyl, wherein said alkyl may be unsubstituted or substituted with a phenyl, halogen, or oxygen. In further embodiments, $R^1$ may be a $C_3$-$C_{10}$ straight, branched, saturated or unsaturated or cyclic alkyl, wherein said alkyl may be unsubstituted or substituted with a phenyl, halogen, or oxygen. In further embodiments, R' may be a $C_{10}$-$C_{20}$ straight, branched, saturated or unsaturated or cyclic alkyl, wherein said alkyl may be unsubstituted or substituted with a phenyl, halogen, or oxygen. In some embodiments, $R^1$ is selected from the group consisting of methyl, ethyl, propyl, butyl, pentyl, hexyl, heptyl, octyl, nonanyl and decyl, with propyl and heptyl being currently preferred.

The group $R^2$—(CH)—O—

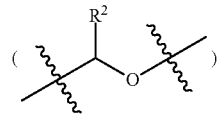

in formula I, which bonded to the $R^1C(=O)$—O— group, is derived from an aldehyde of formula $R^2C(=O)H$, wherein $R^2$ is as defined above. According to some embodiments, the aldehyde is formadehyde (in which case $R^2$ is H). According to other embodiments, the aldehyde is acetaldehyde (in which case $R^2$ is $CH_3$). According to other embodiments, the aldehyde is propionaldehyde (in which case $R^2$ is $CH_2CH_3$). According to other embodiments, the aldehyde is butyrladehyde (in which case $R^2$ is $CH_2CH_2CH_3$).

In further embodiments, $R^2$ is a $C_4$-$C_{10}$ straight, branched, saturated or unsaturated or cyclic alkyl, wherein said alkyl may be unsubstituted or substituted with a phenyl, halogen, or oxygen. In further embodiments, $R^2$ is a $C_1$-$C_{20}$ straight or branched chain alkyl, a $C_2$-$C_{20}$ alkenyl, a $C_2$-$C_{20}$ alkynyl or a $C_3$-$C_{20}$ cycloalkyl, wherein said alkyl, alkenyl, alkynyl or cycloalkyl may be unsubstituted or substituted with a phenyl, halogen, or oxygen. Each possibility represents a separate embodiment of the present invention.

According to some embodiments, $R^3$ is H. In further embodiments, $R^3$ is a nitrogen protecting group selected from Boc and Cbz.

Non-limiting examples of compounds of formula (I) according to the present invention are compounds of formula (A), (B) and (C):

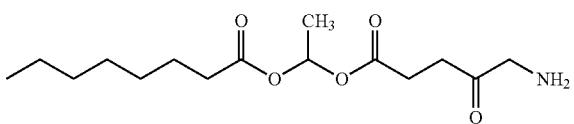
(A)

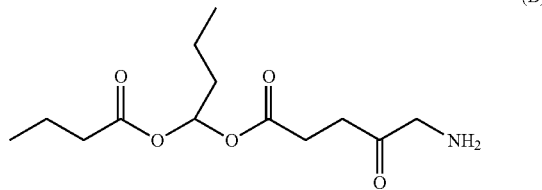
(B)

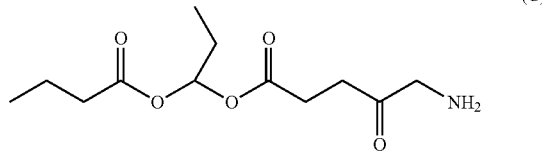
(C)

Compounds A-C are represented by the following chemical names:
1-(Octanoyloxy)ethyl-5-Amino-4-oxopentanoate (A);
1-(Butyryloxy)butyl-5-amino-4-oxopentanoate (B);
1-(Butyryloxy)propionyl-5-amino-4-oxopentanoate hydrochloride (C).

In some embodiments, the compounds of formula (A) to (C) are provided in the form of pharmaceutically acceptable salts, preferaby the hydrochloride (HCl) salts.

According to some embodiments, the compound of formula (I) is a co-drug, wherein upon its hydrolysis (for example, within a target cell) is hydrolyzed to one or more separate compounds/reagents that may exert a biological effect in the target cell. For example, upon introduction of a compound of formula (I) to a cell, the compound may be hydrolyzed (for example by cellular esterases) to produce 5-ALA, a carboxylic acid compound and an aldehyde compound. In some embodiments, one or more of the separate compounds may be active in the cell, that is, they may exert a biological effect in the cell. According to further embodiments, the administration/introduction of the co-drug to the cell may result in enhanced and improved activity of the compounds as compared to introduction of the separate compounds into the cells, when not on the same molecule (co-drug).

According to some embodiments, the carboxylic acid may be a $C_1$-$C_{20}$ straight, branched, saturated or unsaturated or cyclic alkyl, wherein the alkyl may be unsubstituted or substituted with a phenyl, halogen or oxygen, -carboxylic acid. For example, the carboxylic acid may be a HOOC—$CH_2CH_2$—CO—$CH_2$—NH—$R^3$, wherein $R^3$ may be H or a nitrogen protecting group. For example, the carboxylic acid may be HOOC—$CH(NHCOCH_3)CH_2$—SH. In some embodiments the carboxylic acid may inhibit histone deacetylase activity (that is, the carboxylic acid may be an HDACI).

According to some embodiments, the aldehyde may be formaldehyde. For example, the aldehyde may be a $C_1$-$C_{20}$ straight, branched, saturated or unsaturated, or cyclic alkyl.

According to some embodiments, upon introduction of a compound of Formula (I) into a cell, the co-drug may be hydrolyzed to produce a 5-ALA, octanoic acid and formaldehyde. For example, upon introduction of a compound of Formula (I) into a cell, the co-drug may be hydrolyzed to produce a 5-ALA, octanoic acid and acetaldehyde. For example, upon introduction of a compound of Formula (I) into a cell, the co-drug may be hydrolyzed to produce a 5-ALA, decanoic acid and formaldehyde. For example, upon introduction of a compound of Formula (I) into a cell, the co-drug may be hydrolyzed to produce a 5-ALA, decanoic acid and acetaldehyde. For example, upon introduction of a compound of Formula (I) into a cell, the co-drug may be hydrolyzed to produce a 5-ALA, valeric acid and formaldehyde. For example, upon introduction of a compound of Formula (I) into a cell, the co-drug may be hydrolyzed to produce a 5-ALA, valeric acid and acetaldehyde. For example, upon introduction of a compound of Formula (I) into a cell, the co-drug may be hydrolyzed to produce a 5-ALA, 4-phenylbutyric acid and formaldehyde. For example, upon introduction of a compound of Formula (I) into a cell, the co-drug may be hydrolyzed to produce a 5-ALA, 4-phenylbutyric acid and acetaldehyde. For example, upon introduction of a compound of Formula (I) into a cell, the co-drug may be hydrolyzed to produce a 5-ALA, hexanoic acid and acetaldehyde. For example, upon introduction of a compound of Formula (I) into a cell, the co-drug may be hydrolyzed to produce a 5-ALA, retinoic acid and formaldehyde. For example, upon introduction of a compound of Formula (I) into a cell, the co-drug may be hydrolyzed to produce a 5-ALA, retinoic acid and acetaldehyde. Each possibility represents a separate embodiment of the present invention.

According to some embodiments, when $R^1COO$ is derived from hexanoic, $R^2$ is not H. According to other embodiments, when $R^1COO$ is derived from 4-phenylbutyric acid, $R^2$ is not H. According to other embodiments, when $R^1COO$ is derived from pivalic, butyric, valproic, hexanoic, or 4-phenylbutyric acid, $R^2$ is not H. According to other embodiments, when $R^1COO$ is derived pivalic, butyric or valproic acids, $R^2$ is not $CH_3$.

According to some embodiments, the compounds represented by formula (I) may be used to inhibit growth of target cells and/or to kill target cells. The target cells may be any type of cell. In some embodiments, the target cells are cancer cells. In some embodiments, the target cells are non-cancer cells.

According to some embodiments, co-drug compounds represented by formula (I), may induce apoptosis of cells, such as, for example, cancer cells or non-cancer cells, into which the co-drug compound has been introduced.

In further embodiments, co-drug compounds represented by formula (I), may induce down regulation of proteasome expression and activity in cells, which may further lead to accumulation of ubiquitinated proteins and rapid cell death. For example, the cell may be a cancer cell. For example, the cell may be non-cancer cell.

According to some embodiments, the acyloxyalkyl ester co-drugs of formula (I) may provide enhanced antineoplastic effect on cancer cells under photo-irradiation conditions (i.e., PDT dependent) as compared to the effect achieved by the acyloxymethyl ester co-drugs of formula (I). Without wishing to be bound to theory or mechanism, under the PDT conditions, the formaldehyde that may be released in-vivo (within the cancer cells) from the acyloxymethyl ester co-drugs of formula (I) may specifically interrupt with PpIX biosynthesis, highest levels of which enhance the PDT.

According to additional embodiments, the acyloxymethyl ester co-drugs of formula (I) provide enhanced antineoplastic effect on cancer cells under non-PDT conditions as compared to the acyloxyalkyl ester co-drugs of formula (I). Without wishing to be bound to theory or mechanism, under the non-PDT conditions, the formaldehyde that may be released in-vivo (within the cancer cells) from the acyloxymethyl ester co-drugs of formula (I) is able to enhance the production of reactive oxygen species (ROS) in the cells and consequently kill the cells (for example, within 4-96 hours).

According to some embodiments, the compounds of formula (I) may thus be used in the treatment of various types of cancer, in both photodynamic therapy (PDT) and non photodynamic therapy (non-PDT).

Cancer is a disorder in which a population of cells has become, in varying degrees, unresponsive to the control mechanisms that normally govern proliferation and differentiation. Cancer refers to various types of malignant neoplasms and tumors, including metastasis to different sites. Non-limiting examples of cancers which can be treated by the compounds represented by the structure of formula (I) are ovarian cancer, prostate cancer, breast cancer, skin cancer, melanoma, colon cancer, lung cancer, pancreatic cancer, gastric cancer, bladder cancer, Ewing's sarcoma, lymphoma, leukemia, multiple myeloma, head and neck cancer, kidney cancer, bone cancer, liver cancer and thyroid cancer. Specific examples of cancers which the compounds of the present invention are effective at treating or preventing are: adenocarcinoma, adrenal gland tumor, ameloblastoma, anaplastic tumor, anaplastic carcinoma of the thyroid cell, angiofibroma, angioma, angiosarcoma, apudoma, argentaffinoma, arrhenoblastoma, ascites tumor cell, ascitic tumor, astroblastoma, astrocytoma, ataxia-telangiectasia, atrial myxoma, basal cell carcinoma, bone cancer, bone tumor, brainstem glioma, brain tumor, breast cancer, Burkitt's lymphoma, carcinoma, cerebellar astrocytoma, cervical cancer, cherry angioma, cholangiocarcinoma, a cholangioma, chondroblastoma, chondroma, chondrosarcoma, chorioblastoma, choriocarcinoma, colon cancer, common acute lymphoblastic leukemia, craniopharyngioma, cystocarcinoma, cystofibroma, cystoma, cytoma, cutaneous T-cell lymphoma, ductal carcinoma in situ, ductal papilloma, dysgerminoma, encephaloma, endometrial carcinoma, endothelioma, ependymoma, epithelioma, erythroleukaemia, Ewing's sarcoma, extra nodal lymphoma, feline sarcoma, fibroadenoma, fibrosarcoma, follicular cancer of the thyroid, ganglioglioma, gastrinoma, glioblastoma multiforme, glioma, gonadoblastoma, haemangioblastoma, haemangioendothelioblastoma, haemangioendothelioma, haemangiopericytoma, haematolymphangioma, haemocytoblastoma, haemocytoma, hairy cell leukemia, hamartoma, hepatocarcinoma, hepatocellular carcinoma, hepatoma, histoma, Hodgkin's disease, hypernephroma, infiltrating cancer, infiltrating ductal cell carcinoma, insulinoma, juvenile angiofibroma, Kaposi sarcoma, kidney tumor, large cell lymphoma, leukemia, chronic leukemia, acute leukemia, lipoma, liver cancer, liver metastases, Lucke carcinoma, lymphadenoma, lymphangioma, lymphocytic leukemia, lymphocytic lymphoma, lymphocytoma, lymphoedema, lymphoma, lung cancer, malignant mesothelioma, malignant teratoma, mastocytoma, medulloblastoma, melanoma, meningioma, mesothelioma, metastatic cancer, Morton's neuroma, multiple myeloma, myeloblastoma, myeloid leukemia, myelolipoma, myeloma, myoblastoma, myxoma, nasopharyngeal carcinoma, nephroblastoma, neuroblastoma, neurofibroma, neurofibromatosis, neuroglioma, neuroma, non-Hodgkin's lymphoma, oligodendroglioma, optic glioma, osteochondroma, osteogenic sarcoma, osteosarcoma, ovarian cancer, Paget's disease of the nipple, pancoast tumor, pancreatic cancer, phaeochromocytoma, pheochromocytoma, plasmacytoma, primary brain tumor, progonoma, prolactinoma, renal cell carcinoma, retinoblastoma, rhabdomyo sarcoma, rhabdosarcoma, solid tumor, sarcoma, secondary tumor, seminoma, skin cancer, small cell carcinoma, squamous cell carcinoma, strawberry haemangioma, T-cell lymphoma, teratoma, testicular cancer, thymoma, trophoblastic tumor, tumourigenic, vestibular schwannoma, Wilm's tumor, or a combination thereof.

According to some embodiments, there is thus provided a method for the treatment or prevention of cancer, comprising the step of administration to a subject in need thereof a compound represented by formula (I).

In some embodiments, the treatment or prevention of cancer is selected from photodynamic therapy (PDT), non-photodynamic therapy (non-PDT), or a combination thereof.

According to some embodiments, when $R^2$ of the compound of formula (I) is H, the cancer treatment comprises non-photodynamic therapy (non-PDT).

According to further embodiments, when $R^2$ of the compound of formula (I) is a $C_1$-$C_{20}$ straight, branched, saturated or unsaturated, or cyclic alkyl, the cancer treatment comprises photodynamic therapy (PDT).

According to some embodiments, the enhanced effect of co-drugs represented by formula (I) in treatment of cancer cells, may allow the use of lower molar concentration and/or lower light dose (in PDT-dependent treatment) to achieve a desired effect on the cancer cell (i.e., killing the cancer cell, inhibiting it's growth, and the like).

According to some embodiments, octanoic acid is an HDACI that may be used to affect the growth/survival of cancer cells.

In some embodiments, there is thus provided a method for the treatment or prevention of cancer, comprising the step of administering to a subject in need thereof a therapeutically effective amount of octanoic acid or a therapeutically acceptable salt thereof.

According to some embodiments, there are provided compounds of formula (I-a), for use in the treatment or prevention of anemia, wherein the compound(s) of formula (I-a) are represented by the following structure:

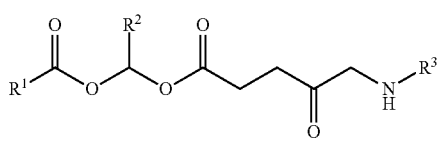

(I-a)

wherein
R$^1$ is
  (a) a C$_1$-C$_{20}$ straight, branched, saturated or unsaturated or cyclic alkyl, wherein said alkyl may be unsubstituted or substituted with a phenyl, halogen, or oxygen;
  (b) —CH$_2$CH$_2$—CO—CH$_2$—NH—R$^3$; or
  (c) —CH(NHCOCH$_3$)CH$_2$—SH;
R$^2$ is a C$_1$-C$_{20}$ straight, branched, saturated or unsaturated, or cyclic alkyl, wherein said alkyl may be unsubstituted or substituted with a phenyl, halogen, or oxygen; and
R$^3$ is H or a nitrogen protecting group;
or a pharmaceutically acceptable salt thereof;
including salts, polymorphs, optical isomers, geometrical isomers, enantiomers, diastereomers, and mixtures thereof.

In some embodiments, the group R$^1$C(=O)—O— is derived from a carboxylic acid of formula R'C(=O)OH, wherein R$^1$ is as defined above. In some embodiments, R$^1$C(=O)O— is derived from a carboxylic acid selected from the group consisting of pivalic, butyric, valeric, hexanoic, 4-phenylbutyric 4-phenylacetic, heptanoic, octanoic, decanoic, and retinoic acid. Currently preferred carboxylic acids are butyric, octanoic, decanoic, valeric or retinoic acid, and a particularly preferred are butyric acid or octanoic acid. Each possibility represents a separate embodiment of the present invention.

According to some embodiments, R$^1$ is a C$_1$-C$_{20}$ straight or branched chain alkyl, a C$_2$-C$_{20}$ alkenyl, a C$_2$-C$_{20}$ alkynyl or a C$_3$-C$_{20}$ cycloalkyl, wherein said alkyl, alkenyl, alkynyl or cycloalkyl may be unsubstituted or substituted with a phenyl, halogen, or oxygen.

According to some embodiments, R$^1$ is a C$_1$-C$_{10}$ straight, branched, saturated or unsaturated or cyclic alkyl, wherein said alkyl may be unsubstituted or substituted with a phenyl, halogen, or oxygen. In further embodiments, R$^1$ may be a C$_5$-C$_{10}$ straight, branched, saturated or unsaturated or cyclic alkyl, wherein said alkyl may be unsubstituted or substituted with a phenyl, halogen, or oxygen. In further embodiments, R$^1$ may be a C$_{10}$-C$_{20}$ straight, branched, saturated or unsaturated or cyclic alkyl, wherein said alkyl may be unsubstituted or substituted with a phenyl, halogen, or oxygen. In some embodiments, R$^1$ is selected from the group consisting of methyl, ethyl, propyl, butyl, pentyl, hexyl, heptyl, octyl, nonanyl and decyl.

The group R$^2$—(CH)—O—

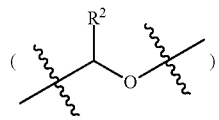

in formula I-a, which bonded to the R$^1$C(=O)—O— group, is derived from an aldehyde of formula R$^2$—C(=O)H, wherein R$^2$ is as defined above. According to some embodiments, the aldehyde is formadehyde (in which case R$^2$ is H). According to other embodiments, the aldehyde is acetaldehyde (in which case R$^2$ is CH$_3$). According to other embodiments, the aldehyde is propionaldehyde (in which case R$^2$ is CH$_2$CH$_3$). According to other embodiments, the aldehyde is butyrladehyde (in which case R$^2$ is CH$_2$CH$_2$CH$_3$).

According to some embodiments, R$^2$ is a C$_1$-C$_{20}$ straight or branched chain alkyl, a C$_2$-C$_{20}$ alkenyl, a C$_2$-C$_{20}$ alkynyl or a C$_3$-C$_{20}$ cycloalkyl, wherein said alkyl, alkenyl, alkynyl or cycloalkyl may be unsubstituted or substituted with a phenyl, halogen, or oxygen. In further embodiments, R$^2$ is a C$_4$-C$_{10}$ straight, branched, saturated or unsaturated or cyclic alkyl, wherein said alkyl may be unsubstituted or substituted with a phenyl, halogen, or oxygen. Each possibility represents a separate embodiment of the present invention.

According to some embodiments, R$^3$ is H. In further embodiments, R$^3$ is a nitrogen protecting group selected from Boc and Cbz.

Non-limiting examples of compounds of formula (I-a) according to the present invention are compounds of formula (A), (B) and (C) as shown above, and further compounds of formula (D) to (G), as shown hereinbelow:

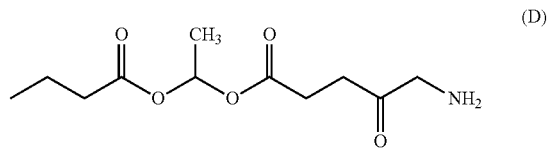

(D)

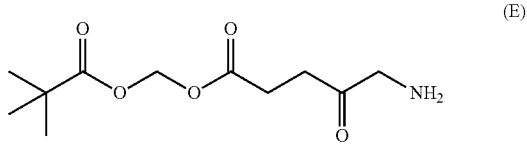

(E)

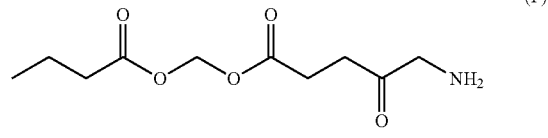

(F)

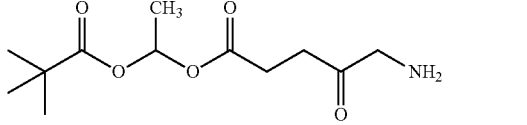

(G)

Compounds D-G are represented by the following chemical names:
1-(butyryloxy)ethyl 5-amino-4-oxopentanoate (D);
(pivaloyloxy)methyl 5-amino-4-oxopentanoate (E);
(butyryloxy)methyl 5-amino-4-oxopentanoate (F);
1-(pivaloyloxy)ethyl 5-amino-4-oxopentanoate (G).

In some embodiments, the compounds of formula (D) to (G) are provided in the form of pharmaceutically acceptable salts, preferably the hydrochloride (HCl) salts.

According to some embodiments, a compound represented by formula (I-a) is a co-drug, wherein upon its hydrolysis (for example, within a target cell) it is hydrolyzed to one or more separate compounds/reagents that may exert a biological effect in the target cell. For example, upon introduction of a compound of formula (I-a) to a cell, the compound may be hydrolyzed (for example by cellular esterases) to produce 5-ALA, carboxylic acid compound and aldehyde compound. In some embodiments, one or more of the separate compounds may be active in the cell, that is, they may exert a biological effect in the cell. According to further embodiments, the administration/introduction of the co-drug to the cell may result in enhanced and improved activity of the compounds as compared to introduction of the separate compounds or a mixture thereof into the cells, when not on the same molecule (co-drug).

According to some embodiments, the carboxylic acid may be a $C_1$-$C_{20}$ straight, branched, saturated or unsaturated or cyclic alkyl, wherein the alkyl may be unsubstituted or substituted with a phenyl, halogen or oxygen, -carboxylic acid. For example, the carboxylic acid may be a HOOC—$CH_2CH_2$—CO—$CH_2$—NH—$R^3$, wherein $R^3$ may be H or a nitrogen protecting group. For example, the carboxylic acid may be HOOC—CH(NHCOCH$_3$)CH$_2$—SH. In some embodiments, the carboxylic acid may inhibit Histone deacetylase activity (that is, the carboxylic acid may be an HDACI).

According to some embodiments, the aldehyde may be a $C_1$-$C_{20}$ straight, branched, saturated or unsaturated, or cyclic alkyl. In some embodiments, the aldehyde is not formaldehyde.

According to some embodiments, upon introduction of a compound of Formula (I-a) into a cell, the co-drug may be hydrolyzed to produce 5-ALA, butyric acid and acetaldehyde. For example, upon introduction of a compound of Formula (I-a) into a cell, the co-drug may be hydrolyzed to produce 5-ALA, valeric acid and acetaldehyde. For example, upon introduction of a compound of Formula (I-a) into a cell, the co-drug may be hydrolyzed to produce 5-ALA, valproic acid and acetaldehyde. For example, upon introduction of a compound of Formula (I-a) into a cell, the co-drug may be hydrolyzed to produce 5-ALA, hexanoic acid and acetaldehyde. For example, upon introduction of a compound of Formula (I-a) into a cell, the co-drug may be hydrolyzed to produce 5-ALA, octanoic acid and acetaldehyde. For example, upon introduction of a compound of Formula (I-a) into a cell, the co-drug may be hydrolyzed to produce 5-ALA, decanoic acid and acetaldehyde. For example, upon introduction of a compound of Formula (I-a) into a cell, the co-drug may be hydrolyzed to produce 5-ALA, 4-phenylbutyric acid and acetaldehyde. For example, upon introduction of a compound of Formula (I-a) into a cell, the co-drug may be hydrolyzed to produce 5-ALA, phenylacetic acid and acetaldehyde. For example, upon introduction of a compound of Formula (I-a) into a cell, the co-drug may be hydrolyzed to produce a 5-ALA, retinoic acid and formaldehyde. For example, upon introduction of a compound of Formula (I-a) into a cell, the co-drug may be hydrolyzed to produce a 5-ALA, retinoic acid and acetaldehyde. Each possibility represents a separate embodiment of the present invention.

According to some embodiments, the compounds represented by the formula (I-a) are able to augment erythropoiesis. Without wishing to be bound to theory or mechanism, stimulation of erythropoiesis may be achieved by two pathways: a) by a direct effect on erythroid progenitors; and/or b) indirectly, by stimulating the function and production/secretion of Erythropoietin (EPO).

According to some embodiments, compounds represented by formula (I-a) are able to induce a dramatic and unexpected change in erythropoiesis and hemoglobin production. As detailed above, a co-drug represented by formula (I-a) may be hydrolyzed in-vivo to one or more active compounds, such as, for example, 5-ALA and a carboxylic acid compound (that may be active as an HDACI). Moreover, as further exemplified hereinbelow, the effect of the co-drug on inducing erythropoiesis and hemoglobin production in a target cell is enhanced as compared to introducing the cell with a 5-ALA or with an HDACI, or even compared to introducing the cell with a mixture of 5-ALA and HDACI. Thus, introducing a target cell with a compound represented by formula (I-a) provide synergistic results with respect to erythropoiesis and hemoglobin production as compared to introducing the cells with compounds such as, 5-ALA, HDACI or a mixture thereof.

According to some embodiments and as further exemplified herein below, a co-drug represented by formula (I-a) is able to induce a synergistic effect on the synthesis of the protoporphirin IX (PpIX), which is generated in an early stage of the heme biosynthetic pathway. The effect on the synthesis of PpIX by a co-drug represented by formula (I-a) is enhanced as compared to the effect on the synthesis of PpIX exerted by 5-ALA alone, HDACI alone or a mixture of 5-ALA and HDACI.

According to some embodiments and as further exemplified hereinbelow, a co-drug represented by formula (I-a) is able to induce the activity of porphobilinogen deaminase (PBGD), which is a key rate-limiting enzyme in the heme biosynthesis pathway. Evaluation of PBGD activity showed that co-drug of 5-ALA and HDACI was more efficient in elevating PBGD activity. The effect on the activity of PBGD by a co-drug represented by formula (I-a) is enhanced as compared to the effect on the activity of PBGD exerted by 5-ALA alone, HDACI alone or a mixture of 5-ALA and HDACI.

According to some embodiments and as further exemplified hereinbelow, a co-drug represented by formula (I-a) is able to induce the expression of Ferrochelatase, which is the enzyme that catalyzes the final step in the heme biosynthetic pathway. Evaluation of Ferrochelatase protein expression showed that co-drug of 5-ALA and HDACI was more efficient in elevating Ferrochelatase activity. The effect on the activity of Ferrochelatase by a co-drug represented by formula (I-a) is enhanced as compared to the effect on the activity of Ferrochelatase exerted by 5-ALA alone, HDACI alone or a mixture of 5-ALA and HDACI.

According to further embodiments, and as further exemplified hereinbelow, a co-drug represented by formula (I-a) is able induce a marked increase of total heme content in treated cells. The increase in the total heme content is significantly higher in cells introduced with a co-drug represented by formula (I-a), as compared to cells introduced with 5-ALA alone, HDACI alone or a mixture of 5-ALA and HDACI.

According to additional embodiments, and as further exemplified hereinbelow, a co-drug represented by formula (I-a) is able to induce expression of globin genes, such as, for example, the α-globin gene. The elevation in expression of the globin genes is significantly higher in cells introduced with a co-drug represented by formula (I-a), as compared to the effect induced by 5-ALA alone, HDACI alone or a mixture thereof.

According to further embodiments, and as further exemplified hereinbelow, a co-drug represented by formula (I-a) is able to induce differentiation of erythroids, which may thereby result in increase in erythropoiesis due to increase in mature red blood cells.

According to some embodiments, there is thus provided a method for the treatment or prevention of anemia, comprising the step of administering to a subject in need thereof a compound represented by the structure of formula (I-a), or a pharmaceutical composition comprising such compound.

In some embodiments, there is provided a method for inducing erythropoiesis, comprising the step of administering to a subject in need there of a compound represented by the structure of formula (I-a), or a pharmaceutical composition comprising such compound.

According to some embodiments, there is provided a method for the treatment or prevention of anemia by inducing erythropoiesis, comprising the step of administering to a subject in need thereof a compound represented by the structure of formula (I-a), or a pharmaceutical composition comprising such compound.

According to some embodiments, the compounds of Formula (I) and Formula (I-a) may be prepared by various methods. For example, the compounds of Formula (I) and Formula (I-a) may be produced according to the general scheme presented in FIG. 1.

As used herein, "pharmaceutical composition" means therapeutically effective amounts of the compounds of the present invention, together with suitable diluents, preservatives, solubilizers, emulsifiers, adjuvant and/or carriers. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Further included are particulate compositions coated with polymers (e.g., poloxamers or poloxamines). Other embodiments of the compositions of the invention incorporate particulate forms, protective coatings, inhibitors or permeation enhancers for various routes of administration, including parenteral, topical, pulmonary, nasal and oral. In some embodiments, the pharmaceutical composition is administered parenterally, paracancerally, transmucosally, transdermally, intramuscularly, intravenously, intradermally, subcutaneously, intraperitonealy, intraventricularly, intracranially or intratumorally.

Moreover, as used herein "pharmaceutically acceptable carriers" are well known to those skilled in the art and include, but are not limited to phosphate buffer and/or saline. Additionally, such pharmaceutically acceptable carriers may be aqueous or non-aqueous solutions, suspensions, and emulsions.

Parenteral vehicles may include, for example, sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present.

In yet another embodiment, the pharmaceutical composition can be delivered in a controlled release system.

The pharmaceutical preparation may comprise one or more of the compounds represented by the structure of formula (I) or formula (I-a), or may further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The preparation can also be administered by intravenous, intra-arterial, or intramuscular injection of a liquid preparation, oral administration of a liquid or solid preparation, or by topical application. Administration can also be accomplished by use of a rectal suppository or a urethral suppository.

The pharmaceutical preparations can be prepared by known dissolving, mixing, granulating, or tablet-forming processes.

The preparation of pharmaceutical compositions which contain an active component is well understood in the art. Typically, such compositions are prepared as aerosols of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients that are pharmaceutically acceptable and compatible with the active ingredient. Suitable excipients are, for example, water, saline, dextrose, glycerol, ethanol, or the like and combinations thereof.

In addition, if desired, the composition can contain minor amounts of auxiliary substances such as wetting or emulsifying agents, pH buffering agents, which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, methanesulfonic, benzene sulfonic, naphthalene sulfonic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In another embodiment, the active compound can be delivered in a vesicle, such as, for example, a liposome.

For topical administration to body surfaces using, for example, creams, ointments, gels, lotions, solutions, co-solvent solutions, suspensions, and the like. The compounds of the present invention or their physiologically tolerated derivatives such as salts, hydrates, and the like are conveniently prepared and applied as solutions, suspensions, or emulsions in a physiologically acceptable diluent with or without a pharmaceutical carrier.

According to yet further embodiments, the compounds of formula (I) or (I-a) may be used in cosmetic treatments;

wherein the compounds may be formulated for topical administration and may be administered to body surface of a subject. The body surface may include, for example, the subject's skin. In some embodiments, the cosmetic treatment may include the use of light irradiation that may be performed after the topical formulation comprising the compounds of formula (I) or formula (I-a) are administered to the body surface.

While a number of aspects and some embodiments have been discussed above, those of skill in the art will readily recognize certain modifications, permutations, additions and sub-combinations thereof. It is therefore intended that the following appended claims and claims hereafter introduced be interpreted to include all such modifications, permutations, additions and sub-combinations as are within their true spirit and scope.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1A

Preparation of Compounds of Formula (I) and Formula (I-a)

The preparation of compounds of Formula (I) and formula (I-a) is performed according to the scheme shown in FIG. 1:

Preparation of Chloroalkyl Esters 4:

To a stirred solution of an acyl chloride (compound 2 in FIG. 1, ($R^1$ is other than H)) and a catalytic amount of a Lewis acid (anhydrous zinc chloride), under a nitrogen atmosphere, an aldehyde (compound 3 in FIG. 1) is dropwise added. The solution is stirred for several hours while the reaction progress is monitored by TLC/HPLC. Upon detection of complete consumption of either the acyl halide (compound 2) or the aldehyde (compound 3), the reaction mixture is filtered through silica gel and the residual chloroalkyl ester product (compound 4) is purified by chromatography or distillation.

Preparation of Compound 6 (i.e., a Compound of Formula (I) or (I-a) Wherein $R^3$ Nitrogen Protecting Group):

To an equimolar mixture of a compound of Formula 5 ($R^3$=nitrogen protecting group such as Boc, CBZ etc.) and a chloroalkyl ester of Formula 4, a tertiary base (triethylamine, N-methylmorpholine, ethyl-diisopropyl amine, 1,8-diazabicycloundec-7-ene (DBU), or 4-dimethylaminopyridine) is added in a dry inert solvent (methylene chloride, methylethyl ketone, chloroform, toluene, ethyl acetate or acetonitrile). The mixture is stirred and heated while the reaction progress is monitored by TLC/HPLC. Upon detection of complete consumption of either compound of Formula 4 or compound of Formula 5, the reaction mixture is filtered, the filtered salt is washed with ethyl acetate and the combined filtrate is evaporated. The residue is dissolved in ethyl acetate and is washed with saturated aqueous sodium bicarbonate and brine, and the organic phase is dried over magnesium sulfate or calcium chloride and the solvent is evaporated. The residue is purified by chromatography to give the product of Formula 6.

Preparation of Compound 7 (i.e., a Compound of Formula (I) or (I-a) Wherein $R^3$=H):

An N-Boc-protected compound of Formula 6 is dissolved in ice-cold ethyl acetate and is treated with a freshly prepared solution of an acid such as hydrogen chloride in ethyl acetate. The reaction progress is monitored by TLC/HPLC and upon detection of complete consumption of 6 the solvent is evaporated to give the salt of formula (7).

When a CBZ-protected compound of Formula 6 is used, the CBZ group is removed by Pd catalyzed hydrogenolysis in the presence of an acid HX (e.g., hydrochloric acid, HCl) dissolved in a suitable solvent (methanol). The reaction progress is monitored by TLC/HPLC and upon detection of complete consumption of 6 the mixture is filtered, and the filtrate is evaporated to give the salt of formula (7).

Example 1B

Preparation of Exemplary Compounds 1-(Octanoyloxy)ethyl-5-Amino-4-oxopentanoate Hydrochloride (A); 1-(Butyryloxy)butyl-5-amino-4-oxopentanoate Hydrochloride (B) and 1-(Butyryloxy)propionyl-5-amino-4-oxopentanoate hydrochloride (C)

General Procedure A:

Coupling 5-(tert-Butoxycarbonylamino)-4-oxopentanoic Acid with Chloroalkyl Esters. A mixture of 5-(tert-butoxycarbonylamino)-4-oxopentanoic acid, (1.2 equiv.) and a chloromethyl/chloroethyl ester (1 equiv.) in dry methyl ethyl ketone under $N_2$ was stirred while triethylamine or DBU (1.2 equiv) was added dropwise. The mixture was refluxed (<80° C.) overnight when using chloromethyl esters or for 2 days in the case of chloroethyl esters. A white precipitate which formed was filtered and washed with EtOAc, and the filtrate was evaporated. The residue was dissolved in EtOAc and was washed with saturated $NaHCO_3$ (×3) and brine (×3), dried over $Na_2SO_4$, filtered, and evaporated. The crude product was purified by flash chromatography.

General Procedure B:

Removal of N-tert-Boc Group. To an ice-cold solution of an N-Boc protected compound in EtOAc was added a freshly prepared solution of 4 N HCl in EtOAc obtained by addition of acetyl chloride to a solution of EtOH in EtOAc, or by gaseous HCl in dry ether. The ice bath was removed after 1 h, and the solution was allowed to warm to room temperature. The reaction was monitored by TLC (hexane/EtOAc, 2.5:1) and was generally completed within a few hours. The solvent was evaporated to give the crude product. The latter was dissolved in MeOH, treated with activated charcoal, and filtered. The filtrate was evaporated and dried under high vacuum to give the product as a semisolid oil/foam.

Preparation of 1-(Octanoyloxy)ethyl-5-amino-4-oxopentanoate Hydrochloride

The compound was prepared as described in Procedures A and B above from 2-chloroethyloctanoate and 5-(tert-butoxycarbonylamino)-4-oxopentanoic acid. $^1$H-NMR (300 MHz, $CDCl_3$) ppm δ 0.87 (t, J=7.20 Hz, 3H, CH2Me), 1.27 (m, 8H, $(CH_2)_4CH_2CH_2CO_2$), 1.45 (d, J=5.40 Hz, 3H, $OCH(CH_3)O$), 1.58 (sext, J=7.32 Hz, 2H, $CH_2CH_2CH_2CO_2$), 2.28 (t, J=7.30 Hz, 2H, $CH_2CH_2CH_2CO_2$), 2.66 ("t", 2H, $COCH_2CH_2CO_2$), 2.94 ("t", 2H, $COCH_2CH_2CO_2$), 4.28 (s, 2H, $CH_2NH_2$), 6.83 (q, J=5.60 Hz, 1H, OCHO).

Preparation of 1-(Butyryloxy)butyl-5-amino-4-oxopentanoate Hydrochloride

The compound was prepared as described in Procedures A and B above from 2-chlorobutylbutyrate and 5-(tert-butoxycarbonylamino)-4-oxopentanoic acid. $^1$H-NMR (300 MHz, CD$_3$OD) ppm δ 0.95+0.96 (two t, J=6.6 Hz, 6H, two Me), 1.65 (m, 6H, CH3CH$_2$CH$_2$CO$_2$+CH$_3$CH$_2$CH$_2$CH), 2.27 (t, J=10.8 Hz, 2H, CH$_2$CH$_2$CH$_2$CO$_2$), 2.70 ("t", 2H, COCH$_2$CH$_2$CO$_2$), 2.87 ("t", 2H, COCH$_2$CH$_2$CO$_2$), 4.02 (s, 2H, CH$_2$NH$_2$), 6.72 (t, J=8.4 Hz, 1H, OCHO).

Preparation of 1-(Butyryloxy)propionyl-5-amino-4-oxopentanoate Hydrochloride

The compound was prepared as described in Procedures A & B from 2-chloroethylbutyrate and 5-(tert-butoxycarbonylamino)-4-oxopentanoic acid. $^1$H-NMR (300 MHz, CD$_3$OD) ppm δ 0.95 (t, J=7.5 Hz, 6H, two Me), 1.61 (sextet, 2H, J=7.5 Hz, CH$_3$CH$_2$CH$_2$CO$_2$), 1.78 (quint, J=5.7 Hz, 2H, CH$_3$CH$_2$CH) (t, J=7.2 Hz, 2H, CH$_3$CH$_2$CH$_2$CO$_2$), 2.70 (m, 2H, COCH$_2$CH$_2$CO$_2$), 2.86 (m, 2H, COCH$_2$CH$_2$CO$_2$), 4.04 (s, 2H, CH$_2$NH$_2$), 6.72 (t, J=5.7 Hz, 1H, OCHO)

Examples 2-14

Biological Effect of Compounds of Formula (I) and Formula (I-a)

Materials and Methods
Erythroid cell line

K-562, a human erythroid-like cell lines were derived from cells explanted from patients with chronic myelogenous leukemia at blast crisis. When induced along the erythroid lineage, the cells accumulate Hb, but fail to express the full erythroid phenotype. Such cells can serve as an experimental model for studying erythroid differentiation and hemoglobin (Hb) synthesis and accumulation at cellular and molecular levels. The cells provide reproducible, uniform, large populations of cells, which can undergo a synchronized differentiation program. Hence, the K-562 cell line may be used to reflect the effect of treatment on erythropoiesis.

Cell Cultures

Myelogenous leukaemia K562 and hepatoma Hep3B cells are grown on tissue culture plates (Greiner, Glos, UK) in RPMI-1640 medium supplemented with 10% fetal calf serum, antibiotics (penicillin-streptomycin-nystatin), and L-glutamine (Biological Industries, Kibbutz Beit-Haemek, Israel). The cells were grown at 37° C. in a humidified atmosphere with 5% CO$_2$, and were re-cultured twice a week.

Human Glioblastoma U251 cells are grown on tissue culture plates (Greiner, Glos, UK) in RPMI-1640 medium supplemented with 10% fetal calf serum, antibiotics (penicillin-streptomycin-nystatin), and L-glutamine (Biological Industries, Kibbutz Beit-Haemek, Israel). The cells are grown at 37° C. in a humidified atmosphere with 5% CO$_2$, and were re-cultured twice a week.

The murine mammary breast carcinoma 4T1 (CRL-2539) and embryonic rat heart H9C2 (CRL-1446) cell lines are obtained (ATCC, Rockville, Md., USA). U251 MG human glioma cell line (Cyagen Bio9sciences) and normal human astrocytes (NHA, Lonza, International). Cells are grown in DMEM with 10% FCS and 2 mM L-glutamine, except the astrocytes that are grown in ABM™ Basal Medium and AGM™ Bullet Kit® (Lonza, International). All cells are grown in the presence of 100 units/mL penicillin, 100 μg/mL streptomycin, 12.5 un/mL nystatin (Biological Industries Beit-Haemek, Israel), and incubated in a humidified atmosphere of 5% CO2 95% air at 37° C.

Cytotoxicity:

Cytotoxicity is evaluated by dual fluorescent staining; propidium iodide (red fluorescence) as a marker for dead (or damaged) cells and fluorescein diacetate (green fluorescence) as a marker for metabolically active cells.

Programmed Cell Death (Apoptosis):

Apoptosis is measured using specific antibodies conjugated to a fluorescence probe (ApopTag, Oncor, Gaithersburg, Md.). Cells are scored by flow cytometry.

Viability Assays:

MTT:

Cells are grown in 24 wells plate in a volume of 0.5 mL and treated as indicated for 96 hours. Then, 77 μL of 5 mg/mL MTT (3-[4,5-dimethylthiazol-2-yl]-2,5-diphenyltetrazolium bromide, (Sigma, Israel)) is added to each well for 2 hours. Afterwards, 400 μL of DMF solution (100 gr SDS dissolved in 250 mL dd H$_2$O with 250 mL of DMF) is added for 4 hours. Absorbance is then measured in 570 nm using a Tecan spectrophotometer (NeoTec, Canada).

Hoechst viability assay is performed as described [12].

Intracellular Heme Assay:

The method for quantitative determination of total heme in cell lysates is performed using hemin as a standard. The "total heme" or "endogenous heme" measured in these assays includes bound and free heme. Following treatments, 100 or 500 μg of cell lysate was added to 100 μL orthotolidine reagent (0.25 gr orthotolidine (Sigma-Aldrich, Israel) dissolved in 80 mL glacial acetic acid (Sigma-Aldrich, Israel) and 10 mL dd H$_2$O). Heme is oxidized to a green product by adding 100 μL of 1.2% H$_2$O$_2$ to the mixture for 10 minutes incubation in the dark. The first oxidation product was further oxidized to a yellow product by adding 0.5 mL of a 1:9 v/v solution of diluted acetic acid. Absorbance of the second product was read at 430 nm using a spectrophotometer (Tecan Trading AG, Switzerland).

Assessment of Cellular PpIX:

Following treatment, cells are harvested, collected by centrifugation, washed twice and resuspended in 0.5 mL with sterile PBS. PpIX fluorescence is measured in 10,000 cells per sample using a FACS (Becton-Dickinson, CA, USA) with an excitation wavelength of 488 nm and emission wavelength>670 nm. Images of the stained cells are examined using a fluorescent microscope (IX70) (Olympus Tokyo, Japan) using an excitation filter of 330-385 nm and barrier filter at 420 nm Western Blotting:

Proteins are quantified and equalized using the Bradford assay (Bio-Rad, CA, USA) and resolved on a 12% polyacrylamide gel. Afterwards, proteins are transferred from the gel onto nitrocellulose membranes (Bio-Rad, CA, USA) using a semi-dry transfer apparatus (Bio-Rad, CA, USA). After blocking the membranes with phosphate-buffered saline+ 0.2% Tween-20 (PBST) (Sigma-Aldrich, Israel) and 5% skim-milk (BD-Diagnostic Systems, MD, USA), membranes are incubated with primary rabbit anti-human PBGD antibody (a generous gift from flemeBiotech, Sweden), or with rabbit anti-α-Hb (H80) (Santa Cruz Biotechnology, CA, USA), or with HRP-conjugated mouse anti-β-actin antibody (C4) (Santa Cruz Biotechnology, CA, USA) diluted in blocking solution for 1 h in room temperature or for overnight in 4° c., washed with PBST and incubated with secondary antibodies diluted in blocking solution. Immuno-reactive proteins were visualized with enhanced chemiluminiscence detection EZ-ECL kit (Biological Industries, Israel) used as recommended by the manufacturer.

Hb and Glycophorin A Immunostaining Analysis by Flow Cytometry:

K562 cells are fixed and stained with primary antibodies anti-αHb or anti-Glycophorin A and are tagged using the compatible secondary antibodies-Alexa 488-conjugated anti-rabbit antibody donkey anti-goat (Invitrogen, Oregon, USA) as recommended by Cell Signaling (MA, USA). Fluorescence is measured in 10,000 cells using FACS with an excitation wavelength of 488 nm and emission wavelength of 530 nm. K562 cells were suspended in paraformaldehyde 4% for 10 min at 37° C., followed by incubation with chilled methanol (final concentration 90%) for 30 min on ice. Cells were washed twice with PBS-/- and blocked with BSA 0.5% in PBS-/- for 10 min at room temperature. Afterwards, the cells were incubated in 50 µL of the primary antibody goat polyclonal Ferrochelatase (Santa Cruz Biotechnology, Santa Cruz, Calif., USA) or goat polyclonal glycophorin A (Santa Cruz Biotechnology, Santa Cruz, Calif., USA) (1:50 in BSA 0.5%) or anti-a Hb for 30 min at room temperature, washed once with PBS-/-, and incubated with a fluorescent donkey anti-goat IgG secondary antibody (1:1000) (Invitrogen, Carlsbad, Calif., USA) for 30 min at room temperature. The cells were washed again with PBS-/- and fluorescence was measured in 10,000 cells per sample using a FACS (Becton-Dickinson, San Jose, Calif., USA) with an excitation wavelength of 488 nm and emission wavelength 530 nm.

RNA Preparation and Concentration Determination

Total RNA was isolated after the cells were harvested using EZ-RNA total RNA isolation kit according to the manufacturer's instructions (Biological Industries). RNA concentration was measured using NanoDrop spectrophotometer.

Globin RNA Accumulation:

Globin RNAs are quantified by quantitative real time polymerase chain reaction, (qRT-PCR) using SYBR I Green (Applied Biosystems). The cDNA is generated from cell culture or tissues using a PCR purification kit (Qiagen, Valencia, Calif., USA). The qRT-PCR is performed in triplicate and is repeated in at least three separate experiments.

Quantitative PCR Amplification

Total RNA (1 µg) was primed by oligo dT and reverse-transcribed by Verso cDNA kit according to the manufacturer's protocol (Thermo Scientific, West Palm Beach, USA). Quantitative PCR was done on a Step One Plus thermocycler (Applied Byosystems, Van Allen Way, CA, USA). The comparative threshold method was used to calculate the relative gene expression. Values were normalized against glyceraldehyde 3-phosphate dehydrogenase (GAPDH) for the different genes. Real time PCR was performed with Syber Green (Kapa Biosystems, Woburn, Mass., USA) using the following primers:

TABLE 1

| HBA1/A2 | Forward 5'-CCGACAAGACCAACGTCA (SEQ ID NO. 1) |
|---|---|
| | Reverse 5'-CGAAGTGCGGGAAGTAGG (SEQ ID NO. 2) |
| PBGD | Forward 5'-ACGAGCAGCAGGAGTTCA (SEQ ID NO. 3) |
| | Reverse 5'-ATGTCCTGGTCCTTGGCT (SEQ ID NO. 4) |

TABLE 1-continued

| GAPDH | Forward 5'-CTTTGGTATCGTGGAAGGACTC (SEQ ID NO. 5) |
|---|---|
| | Reverse 5'-AGTAGAGGCAGGGATGATGTTC (SEQ ID NO. 6) |

Relative quantification of gene expression was determined by the comparative threshold method (ÄCT), as described previously (Livak K J, Schmittgen T D). Analysis of relative gene expression data using real-time quantitative PCR and the 2(-Delta Delta C(T)) Method [18]. Expression of the Gapdh mRNA in each individual sample was used to normalize the dataset.

Hemoglobin Measurements

Samples are added to Drabkin's solution and the hemoglobin content is analyzed colorimetrically at 540 nm in a spectrophotometer (Shimadzu UV 1240). Hemoglobin content calculated curve following manufacturer's instructions.

Erythropoietin (EPO) Measurements

EPO protein level in hepatoma cell line and in kideny is determined by Western blot analysis using rabbit polyclonal IgG antibody against EPO (Santa Cruz, USA) is resolved on a 12% polyacrylamide gel as described above. EPO RNA quantitation: RNA is extracted from cells and subjected to qRT-PCR analysis using StepOnePlus (Applied Biosystem).

PBGD Enzymatic Activity Assay

K562 cells ($1 \times 10^6$) are treated for 96 hours. PBGD activity is assayed as previously described [15] by determining the fluorescence of uroporphyrin formed by the light-induced oxidation of uroporphyrinogen, which is the immediate product of the enzymatic deamination of 4 porphobilinogen molecules. In short, cells are harvested following treatment, and washed twice with PBS. After centrifugation, the pellet was resuspended in 200 µL 50 mM Tris buffer (pH 8.2) with 0.2% Triton. The cells are homogenized on ice and protein levels are quantified using the Bradford method. 400 µg protein was taken out in duplicates for incubation in 300 µL of 50 mM Tris buffer (pH 8.2) containing 0.2% Triton, with final concentration of 85 µM PBG (Sigma, Israel) for 1 hour at 37° C. The reaction is stopped by addition of 1.2 mL 15.6% TCA. The tubes are left open for room light exposure at room temperature for 10 minutes in order to oxidize uroporphyrinogen to uroporphyrin. After 15 minutes centrifugation at 3,300 rpm, 200 µL the supernatant was collected into a black 96 well plate (Greiner Bio one, Germany). The samples fluorescence is read using a Synergy spectrofluorometer (BioTek Instruments, VT, USA) with an excitation wavelength of 404 nm, and an emission wavelength of 595 nm. PBGD specific activity is calculated as activity percentage of control.

HDAC Activity

Inhibition of the activity HDAC class I and II in the cells is performed with the fluorescent kit (AK-503, Biomol, USA). The cells are seeded ($10 \times 10^3$ cells/well) in 96-well plates (in quadruplicates) in growth medium for 24 hours and then treated. Incubation with the HDAC substrate (Fluor de Lys™) is for 2 hours. The reaction is terminated by the addition of Fluor de Lys™ developer and 2 µM trichostatin A (TSA). The % of inhibition is calculated from the ratio of the fluorescence (measured at 355 nm excitation and 460 nm emission) in the treated compared to the untreated control culture.

Histone Acetylation

Quantitative analyses of total Histone (H4 or H3) or specific histone acetylation detection are conducted fresh from frozen tissues, and cultured adherent and suspension cells are conducted using Western blot analysis for total H4 or H3 acetylation is performed as described [9] and for specific histone acetylation a fluorometric kit (Epigenetek, USA) is used.

Photosensitization of the Cells

U251 cells are seeded and incubated with tested compounds for 4 hours in serum-free medium. Cells are irradiated for 10 min using a Vilber-Lourmat light source VL-206BL, delivering a power density of 13 J/cm$^2$ at 360-410 nm (max at 365 nm).

Measurement of ROS

ROS are measured in live cells as intracellular peroxides by monitoring the oxidation of DCF-DA. The membrane-permeable dye undergoes deacetylation by intracellular esterases and oxidation by ROS. Cells ($2\times10^5$) are treated with the tested compounds for 4 hours, and then half the samples are irradiated for 10 min. The samples are incubated with DCF-DA (10 µM) for 30 min at 37° C., washed twice with PBS, and analyzed ($10^4$ cells) by flow cytometry.

Assessment of Mitochondrial Membrane Potential ($\Delta\Psi m$)

The fluorescent mitochondrial-specific cationic dye JC-1 undergoes potential-dependent accumulation in the mitochondria. U251 cells ($2\times10^4$) are seeded in 96-well black plates (Greiner Bio-One, Germany), treated for 4 hours with the tested compounds, and exposed to light irradiation (10 min). Immediately after irradiation, the mitochondrial membrane potential of the cells is measured as previously described [16]. Images of the stained cells were examined using a fluorescent microscope (Nikon TE-2000E), an excitation filter of 450 nm, and a barrier filter at 520 nm.

Apoptosis Assay by FACS Analysis

U251 or K562 cells ($2\times10^5$) are seeded in 60 mm plates and treated with the tested compounds. After an incubation of 4 hours, half of the samples are irradiated for 10 min, and 24 hours later, the cells are trypsinized, double stained with Annexin V-FITC and PI (MEBCYTO Apoptosis kit, MBL, Nagoya, Japan) according to the manufacturer's instructions, and subjected to flow cytometry analysis (FACSCalibur cytometer, Becton Dickinson, N.J.). The percentage of cells is defined by their distribution in a fluorescence dot plot using the flow cytometry analysis software-FlowJo.

Giemsa Staining

U251 cells are seeded on 6 well plates and treated with the tested compounds. Four hours later, half of the samples are irradiated, and 1 hour subsequently the cells were stained with May Grunwald for 5 min, washed with distilled water, and stained for 10 min with Giemsa stain (Sigma-Aldrich, St. Louis, Mo.), prepared as per the manufacturer's instructions. After the cells are washed with distilled water, they are air-dried and observed under a light microscope.

Proteosome Activity Assay

U251 cells ($10^6$) are seeded in 10 cm$^2$ cell culture dishes for 24 hours and then treated with tested compounds for 4 hours and irradiated at light intensity 6.5 J/cm$^2$. The cells are harvested with rubber policemen in PBS, centrifuged, and washed with PBS, and the pellets were resuspended in 300 µL of Tris-base buffer (100 mM, pH 7.5) containing 1% Triton X-100 and homogenized on ice. The lysates (500 µg) are incubated for 1 hour with N-succinyl-Leu-Leu-Val-Tyr-7-amido-4-methylcoumarin (13 µM) (Sigma, St. Louis, Mo.) to measure the chymotrypsin-like activity of the proteasome and Z-Leu-Leu-Glu-β-naphtylamide (100 µM) (Sigma, St. Louis, Mo.) to measure the caspase-like activity of the proteasome. The reaction is stopped by addition of ice-cold ethanol, and the samples are centrifuged for 5 min at 5000 g. The supernatants are collected, and the fluorescence at excitation/emission filters of 390/460 nm was measured by the FluoStar fluorimeter (BMG Labtech, Germany).

In Vivo Studies

In vivo normal Balb-c mice are induced by treatment with the hemolytic agent, phenylhydrazine (Sigma) dissolved at 6 mg/ml in PBS and injected intraperitoneally at 60 mg/kg on two consecutive days. Pre-existing RBCs decayed in the control mice within a week and started to recover by day 4 and all survived and regained a normal hematocrit by day 10. Positive control were mice treated with recombinant human EPO injected intraperitoneally (50 IU/mouse) on 3 consecutive days, tested compounds were injected to the mice at ½; ¼; ⅛; of their MTD. Blood samples drawn at different times points from mice by retro-orbital venipuncture under anesthesia. Hb level, number of red blood cell and reticulocytes, serum EPO and Hb content are determined.

In an additional setting 8 weeks old male Balb-c mice were divided to two groups, Group 1 received 4 mg/kg ip dose of Doxorubicin (Dox) once a week and Group 2 received the same Doxorubicin treatment and in addition the mice were treated with 50 mg/kg ip dose of the tested compound three times a week. Termination was done on day 19, blood samples were drawn by retro-orbital venipuncture under anesthesia. Hemoglobin levels in heparinized whole blood were determined using Drabkints reagent and standard hemoglobin obtained from Sigma-Aldrich and prepared and stored as instructed by the manufacturer.

Syngeneic Murine 4T1 Breast Carcinoma Metastatic Model

Eight- to ten-week old female BALB/c mice are implanted sc with 4T1 mammary carcinoma cells ($5\times10^5$). Tumor volume was measured with a caliper twice a week and calculated by measured lengths (L) and widths (W) using the (L×W$^2$)/2 formula. Treatment commenced when the tumor volume reached a 50-100 mm$^3$. The mice are randomly assigned to treatment groups.

Flank Glioblastoma Xenograft Model

Eight- to ten-week old male HSD athymic FOX Nude mice (Harlan, Israel) are inoculated subcutaneously (sc) in the flank with $5\times10^6$ U251 cells. Treatment commenced when the tumor volume reached a 50-100 mm$^3$. The mice are randomly assigned to treatment groups.

Mice Treatment

The mice are randomized and divided to two arms, one arm is irradiated 3 times/week together with the administration of the tested compounds and the other arm is not. The tested compounds are given at 50 mg/kg and 25 mg/kg by gavage 3 times/week. Tumor volume is measured with a caliper twice a week and calculated by measured lengths (L) and widths (W) using the (L×W$^2$)/2 formula.

Photoirradiation Procedure

A high intensity light delivery system (Vario Ray, SeNET Haifa Israel) for PDT, is used as a light source. The wavelength range (600-700 nm), light energy density per pulse (0.6 J cm$^{-2}$). Prior to the photoirradiation, the mice are anesthetized and are then placed in a special plastic tube. The area of the sc implanted tumor is exposed through a hole and is irradiated. All animal experiments are conducted according to the NCl Laboratory Animal Care Guidelines and with the approval of the Tel Aviv University Committee for Animal Experimentation and the Israel Ministry of Health.

Scanning Electron Microscopy and Transmission Electron Microscopy

Analysis is performed on bone-marrow, spleen and liver, processed as described in [17]. Briefly, cells are treated for 96 hours (hrs), harvested and fixed with Karnovsky fixative. The samples are washed in 0.1 M cacodylate buffer and fixed with 1% OsO$_4$ in 0.1 M sodium cacodylate buffer for 1 hour (h). The samples are then dehydrated in graded ethanol solutions and propylene oxide and embedded in agar mix. Thin sections are cut, stained with uranyl acetate and lead citrate, and observed under a transmission electron microscope.

Immunohistochemistry (IHC) Staining

Immunohystochemistry (IHC) staining of paraffin-embedded blocks of bone marrow, spleen and liver is performed as described [11] and stained for stem/progenitor cell marker CD133, cytochrome-c, Ki67, Epo receptor and c-Kit.

Example 2

Changes in Synthesis of PpIX in K562 Cells in Response to Various Treatments

Figure 2A:
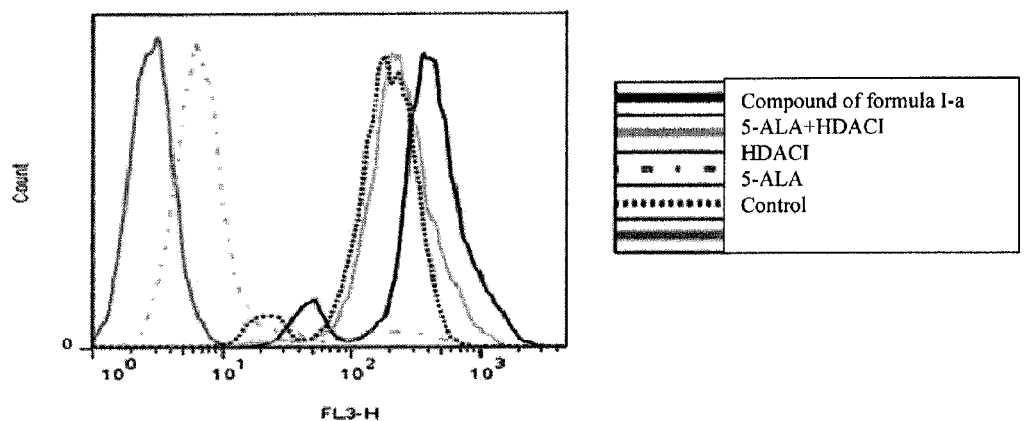
FIGS. 2A-B show the effect of compounds of formula (I-a) on the synthesis of protoporphirin IX (PpIX) in K562 cells.
Figure 2B:
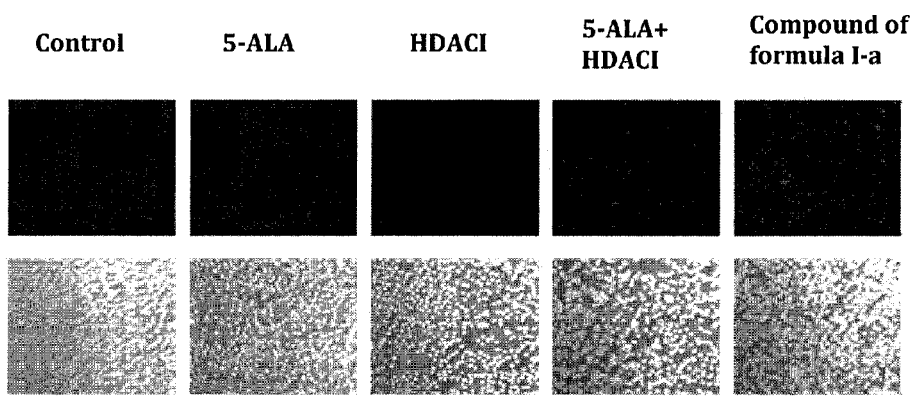

K562 cells are grown as described above and incubated without (control) or with 0.5 mM of various compounds for 96 hours with 5-ALA, HDACI compound (in this example, butyric acid (BA)), a mixture of 5-ALA and an HDACI (BA); and a compound of Formula (I-a) (in this example, 1-(butyryloxy)ethyl-5-amino-4-oxopentanoate, a compound of formula (D) (hereinafter, AlaAcBu)). PpIX fluorescence is measured at the FL-3 channel of FACS Calibur. Additionally, pictures of cells are taken using a fluorescent microscope-Nikon TE200-E, to show PpIX fluorescence. The results are presented in FIGS. 2A-B. FIG. 2A shows a representative histogram depicting the flow cytometry analysis of the various compounds tested. FIG. 2B shows the pictures of cells under various experimental conditions. The results show that the effect exerted by a compound of formula (I-a) (in this example, AlaAcBu), on the intensity of the fluorescence generated by PpIX is substantially higher when compared to the effect exerted by 5-ALA alone, HDACI alone (in this example, BA) or the mixture of the 5-ALA and the HDACI (BA). The results thus suggest that a co-drug of Formula (I-a) (in this example, AlaAcBu), which may be hydrolyzed in the cells to 5-ALA and HDACI (in this example, BA), induces a synergistic effect on the synthesis of protoporphirin IX (PpIX), as compared to the effect by 5-ALA alone, HDACI (BA) alone or even a mixture thereof.

Example 3

Figure 3A:
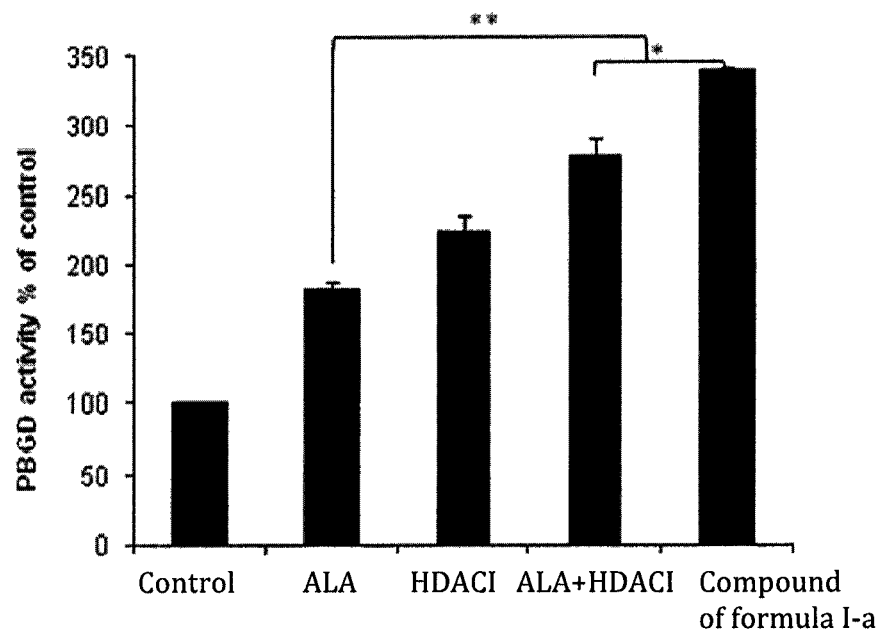
FIGS. 3A-C show the effect of various tested compounds on the activity and synthesis of porphobilinogen deaminase (PBGD) in K562 cells.

Activation of the Key Enzymes in the Heme Biosynthesis Pathway (PBGD and Ferrochelatase) in K562 Cells in Response to Various Treatments K562 cells are grown as described above and incubated with 0.5 mM of various compounds for 96 hours. Activity of PBGD is evaluated as described above. Expression level of the PBGD protein is evaluated using Western blot analysis (as detailed above). Expression level of PBGD mRNA are evaluated using Quantitative real-time PCR. The results are presented in FIGS. 3A-C, respectively. As shown in FIG. 3A, which show a bar graph of the relative activity of PGBD compared to control, the effect of the compound of formula (I-a) (in this example, 1-(butyryloxy)ethyl-5-amino-4-oxopentanoate, (AlaAcBu)), on the activity of PGBD is significantly (**=p<0.05, *=p<0.1) higher compared to the effect on the activity of PGBD exerted by ALA alone, HDACI alone (in this example, BA), or a mixture of ALA and HDACI.

Figure 3B:
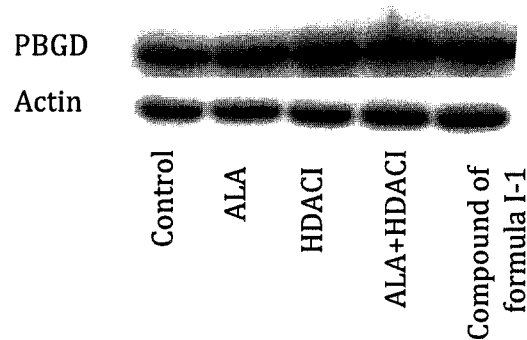
Figure 3C:
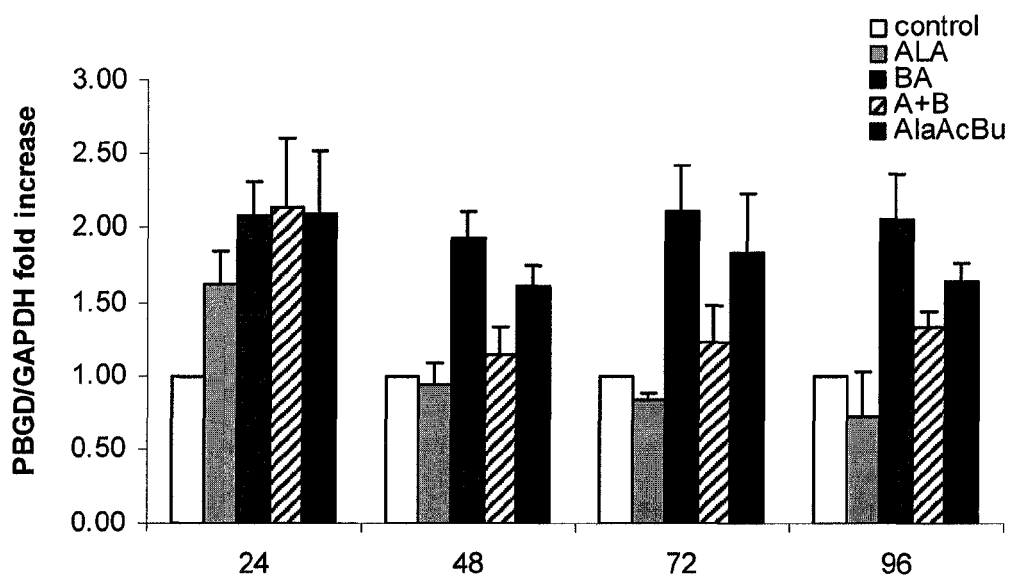

As shown in FIG. 3B, the expression levels of PGBD are increased similarly after 96 hours with all three treatments (i.e. a compound of formula (I-a) (in this example, 1-(butyryloxy)ethyl-5-amino-4-oxopentanoate, (AlaAcBu)), ALA+HDACI (in this example, BA) and HDACI (BA), compared to untreated cells or cells treated with ALA. The results thus suggest that a co-drug of formula (I-a) (in this example, 1-(butyryloxy)ethyl-5-amino-4-oxopentanoate, (AlaAcBu)), which may be hydrolyzed in the cells to 5-ALA and HDACI (BA in this example), induces a synergistic effect on the synthesis and activity of PGBD, as compared to the effect by 5-ALA alone, HDACI alone (BA in this example) or a mixture thereof. As shown in FIG. 3C, which demonstrates quantitative real-time PCR analysis of PBGD mRNA, all the indicated treatments elevated PBGD to the maximum level already after 24 hours incubation (FIG. 3 C). After 48-96 hours PBGD levels following ALA and ALA+HDACI (BA in this example) treatment significantly decreased. These results may indicate that the enhanced activity of PBGD has a greater effect on heme synthesis rather than on it's mRNA or protein expression. As detailed above, since PBGD, which is the third enzyme in the heme biosynthesis pathway, is a rate limiting enzyme in the heme biosynthesis pathway, upregulation of the PBGD activity results in increased biosynthesis of PpIX. The elevated levels of PpIX, result in increased heme levels, which is necessary for hemoglobin synthesis.

Figure 3D:
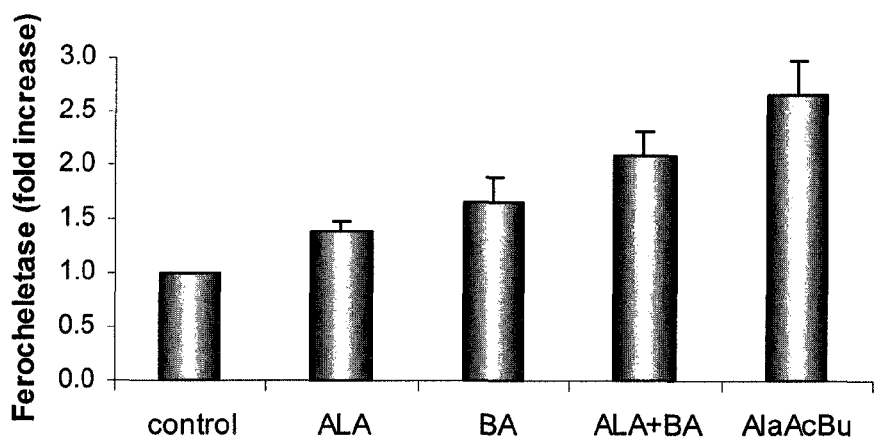
FIGS. 3D-E show the effect of various treatments on the synthesis of Ferrochelatase in K562 cells.
Figure 3E:
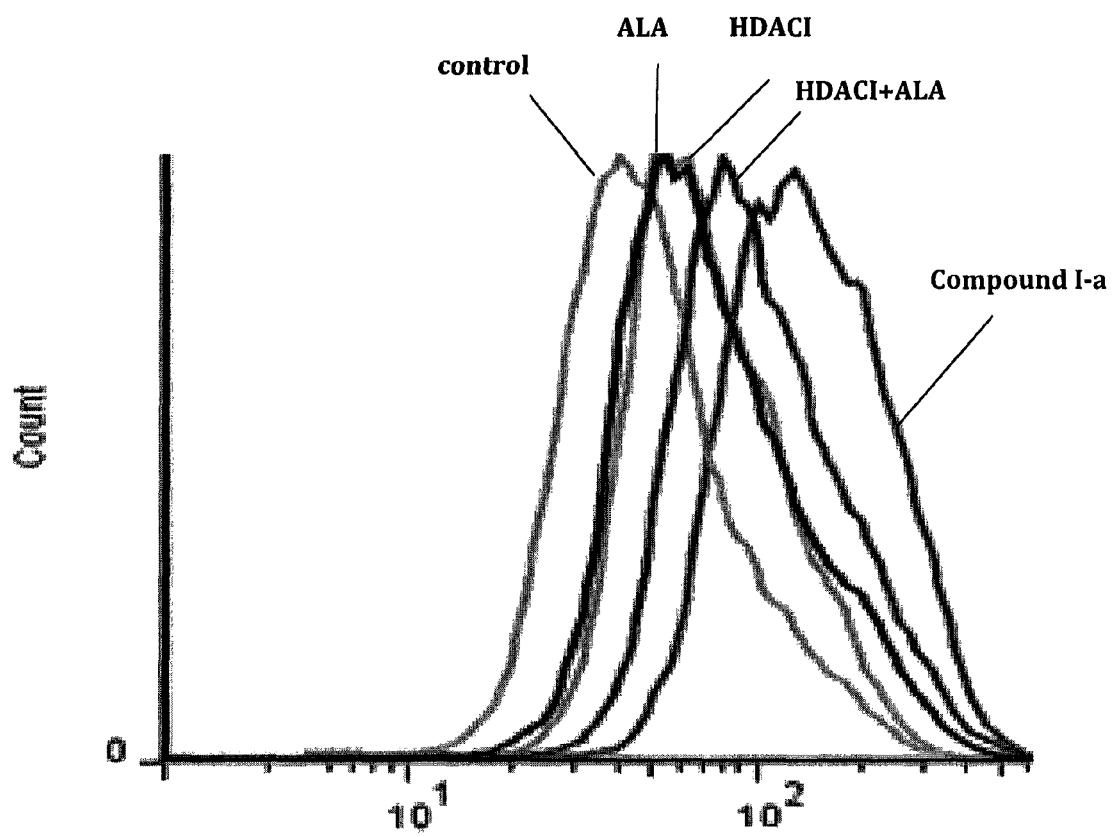

Ferrochelatase is the enzyme that catalyzes the final step in the heme biosynthetic pathway. Reference is now made to FIGS. 3D-E, which shows a bar graph and FACS analysis of expression of Ferrochelatase protein under different experimental conditions, respectively. As shown in FIGS. 3D-E, of formula (I-a) (in this example, AlaAcBu) elevated Ferrochelatase protein expression to a significantly higher level than did ALA, HDACI (in this example, BA) or their mixture. The results thus indicate that AlaAcBu induces an efficient erythroid differentiation also through activation of the key enzymes in the heme synthesis pathway, namely, PBGD and Ferrochelatase.

Example 4

Synthesis of Hemoglobin in K562 Cells in Response to Various Treatments

Figure 4A:
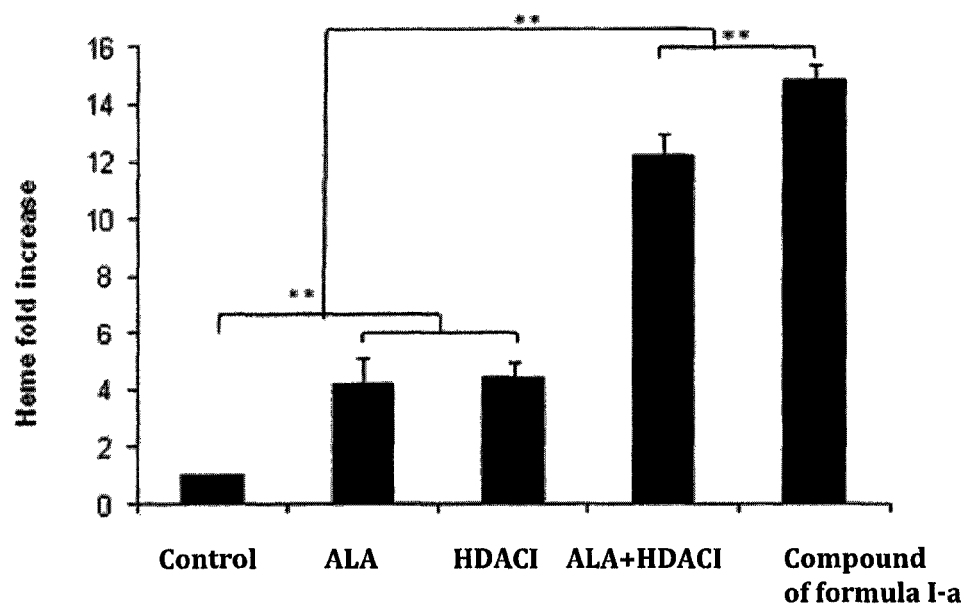
FIGS. 4A-E show the effect of various tested compounds on the synthesis (amount) of hemoglobin.
Figure 4B:
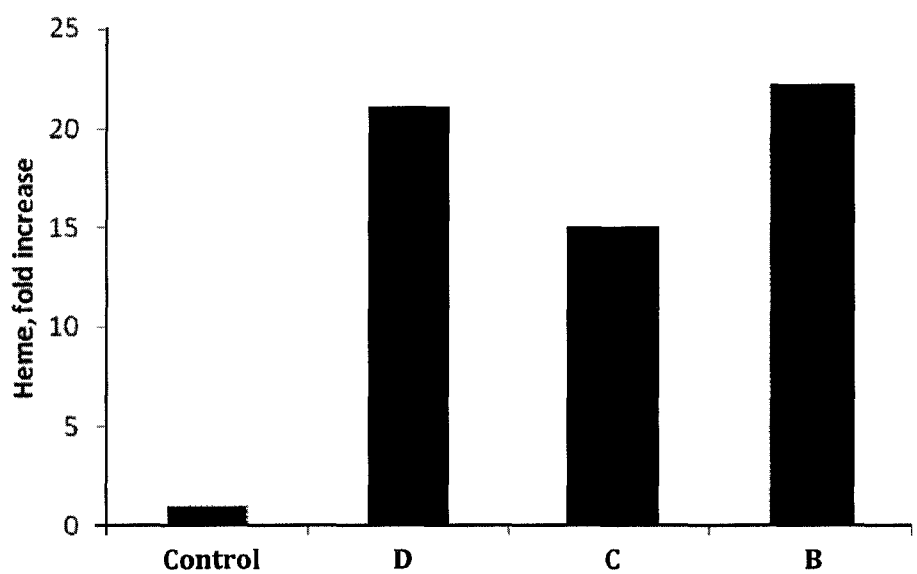
Figure 4C:
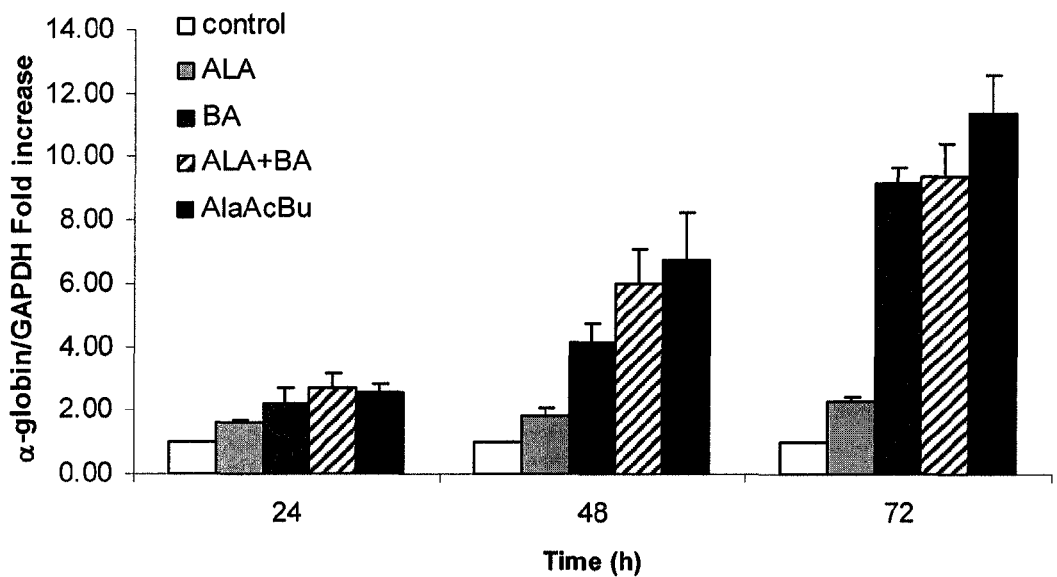
Figure 4D:
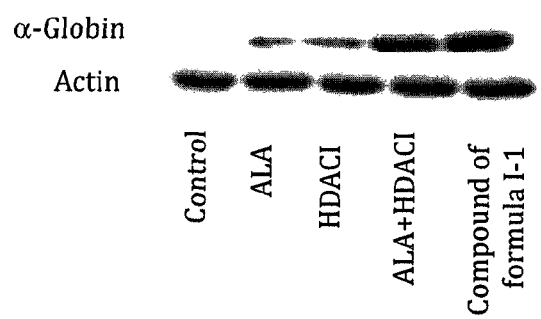
Figure 4E:
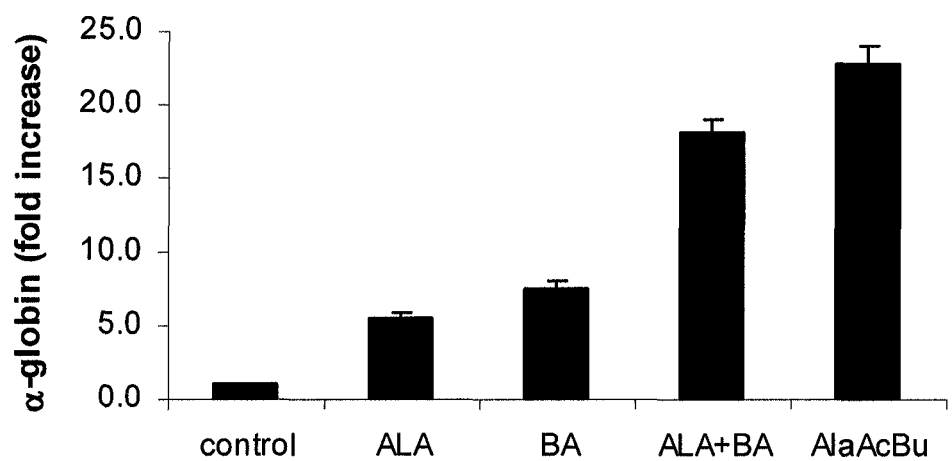

K562 cells are grown as described above and incubated with 0.5 mM of various compounds for 96 hours. Total heme content in the cells is evaluated. In addition, a globin mRNA and protein expression levels are evaluated using Quantitative real-time PCR and Western blot analysis, respectively. The results are presented in FIGS. 4A-E. As shown in FIG. 4A, which shows a bar graph of the fold increase in total heme content, the effect of the compound of formula (I-a) (in this example, 1-(butyryloxy)ethyl-5-amino-4-oxopentanoate, (AlaAcBu)) on the increase of total heme is significantly (**=p<0.005) higher compared to the effect on heme, exerted by ALA alone, HDACI alone (BA in this example) or a mixture of ALA and HDACI (BA). Reference is now made to FIG. 4B, which shows a bar graph of the fold increase in total heme content as compared to control, in response to treatment with 0.25 nM (for 96 hours) with various compounds of formula (I-a): (D), treatment with 1-(butyryloxy)ethyl 5-amino-4-oxopentanoate (AlaAcBu); (C) treatment with 1-(butyryloxy)propionyl-5-amino-4-oxopentanoate hydrochloride, (B) treatment with 1-(butyryloxy)butyl-5-amino-4-oxopentanoate hydrochloride). The results show that the various compounds of formula (I-a) cause 15-22 foled increase of total heme as compared to the control (i.e. cells treated only with vehicle). As shown in FIG. 4C, Quantitative real-time PCR analysis of α-globin demonstrates that the compound of formula (I-a) (in this example, AlaAcBu) significantly elevates α-globin mRNA levels compared to untreated cells and cells that were treated with ALA, HDACI (in this example, BA) or the ALA+HDACI mixture. α-Globin mRNA levels were examined following 24, 48 and 72 hours incubation and reached their peak after 72 hours in which the compound of formula (I-a) (in this example, AlaAcBu) elevated α-globin expression 11.3-fold, significantly (p<0.5) more than did the ALA+HDACI (in this example, BA) mixture (9.3), HDACI (BA) (9.1) or ALA (2.2) alone. As shown in FIGS. 4D-E, which shows Western blot analysis of the protein expression levels of α-globin and quantitation thereof, respectively, the protein expression levels of α-globin are markedly elevated in response to incubating the cells with a compound of formula (I-a) (in this example, 1-(butyryloxy)ethyl-5-amino-4-oxopentanoate, (AlaAcBu)) as compared to any other treatment. The results thus suggest that a co-drug of formula (I-a), which may be hydrolyzed in the cells to 5-ALA and HDACI, induces a synergistic effect on the total heme content in the cells and on the expression of α-globin in the cells, as compared to the effect by 5-ALA alone, HDACI alone or a mixture thereof.

Example 5

Differentiation of Erythroblasts in Response to Various Treatments

Figure 5A:
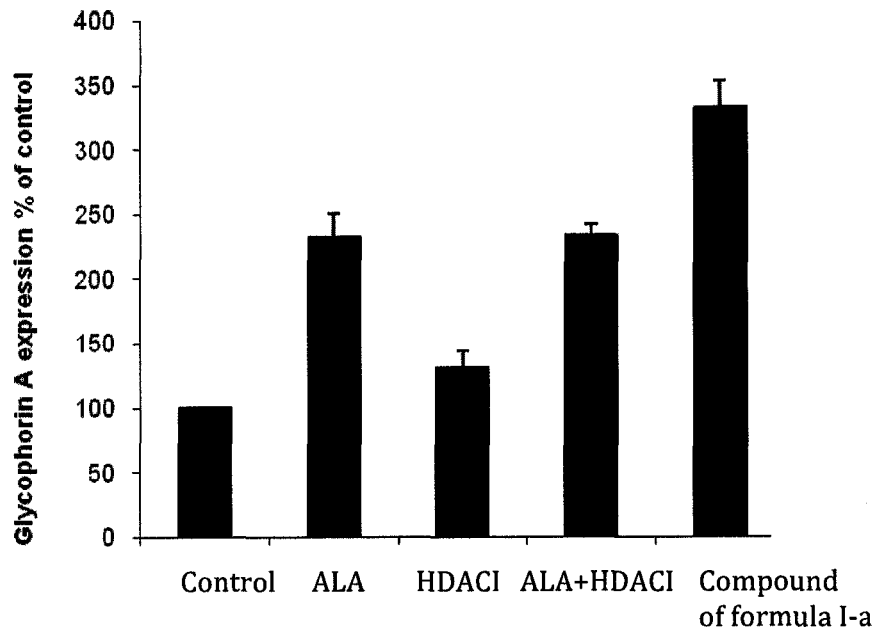
FIGS. 5A-B show the effect of various tested compounds on differentiation of erythroblasts.
Figure 5B:
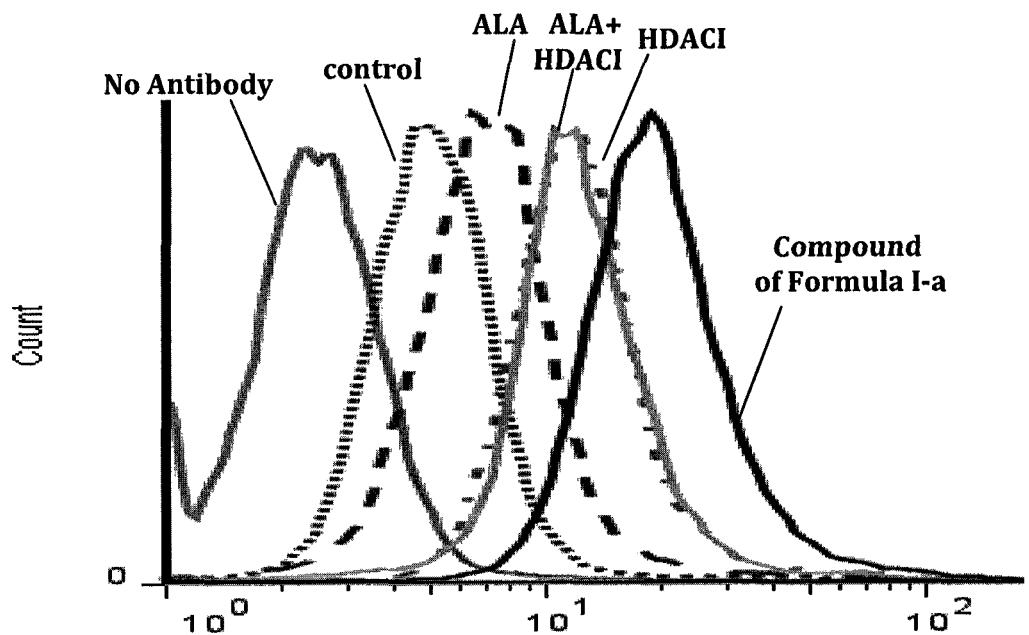

K562 cells are grown as described above and incubated with 0.5 mM of various compounds for 96 hours. Glycophorin A, which is a sialoglycoprotein expressed on the surface of differentiating erythroblast in the process of maturation to red blood cells is a marker of differentiation. Glycophorin A content is measured using immunostaining analyzed by flow cytometry, as detailed above. The results are presented in FIGS. 5A-B. As shown in FIG. 5A, which shows a bar graph of the relative expression of Glycophorin A (as percentage of control), that a co-drug of formula (I-a) (in this example, 1-(butyryloxy)ethyl-5-amino-4-oxopentanoate, (AlaAcBu)) induces the highest increase in the relative expression of the glycophorin A protein as compared to any other treatment. The results represent average values obtained from >3 independent experiments. FIG. 5B shows a representative histogram depicting the flow cytometry analysis. The results thus suggest that a co-drug of formula (I-a) (in this example, AlaAcBu), which may be hydrolyzed in the cells to 5-ALA and HDACI (in this example, BA), induces a synergistic effect on the hematopoietic differentiation of the cells (as determined by expression of Glycophorin A), as compared to the effect by 5-ALA alone, HDACI alone or a mixture thereof.

Example 6

Proliferation Arrest Induced by a Compound of Formula (I-a)

Figure 6A:
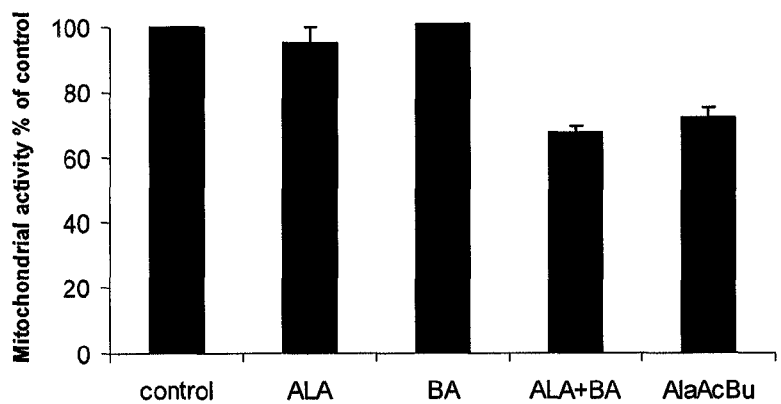
FIGS. 6A-B show the effect of various compounds on K562 cell proliferation.
Figure 6B:
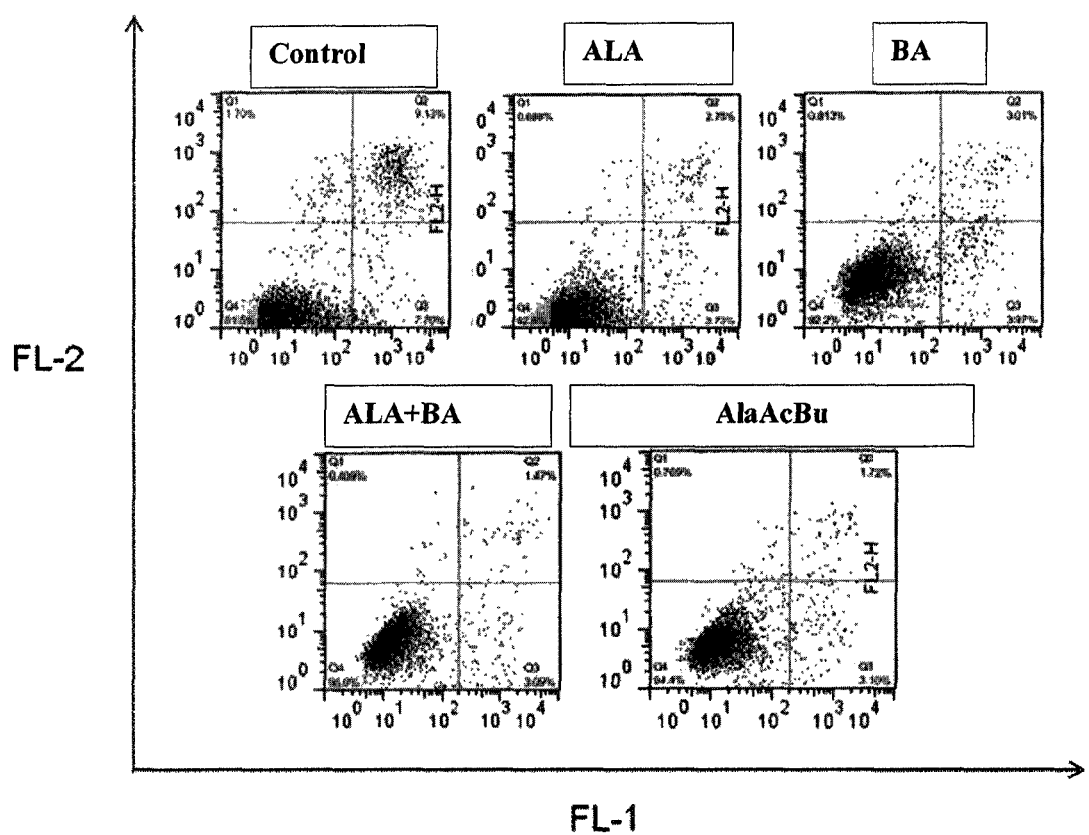

To evaluate the effect of various tested compounds on cell proliferation, K562 cells were treated for 96 hours and their viability was evaluated by MTT as detailed above. The results are presented in FIG. 6A, which shows a bar graph illustrating the mitochondria activity (% of control) under various treatments. As shown in FIG. 6A, a compound of Formula (I-a) (in this example, 1-(butyryloxy)ethyl-5-amino-4-oxopentanoate, (AlaAcBu)) as well as a mixture of ALA+HDACI (in this example, BA), significantly inhibited cell proliferation (33% and 28% inhibition, respectively) while ALA did not affect cell viability and HDACI (BA in this example) even increased it. The results thus indicate that the compound of Formula (I-a) (in this exmaple, AlaAcBu) as well as a mixture of ALA+HDACI (in this example, BA), induce cell mortality, or alternately, decrease proliferation due to cell differentiation. To distinguish between the two possibilities, the cells were double-stained with Annexin V and PI. The results are shown in FIG. 6B, which shows FACS analysisof the cells under different experimental conditions, as indicated. The mortality (necrosis, early and late apoptosis) assessed by FACS revealed that the amount of necrotic/apoptotic cells was unaffected by any of the treatments. Thus, the compounds of formula (I-a) (in this example, AlaAcBu) and the ALA+HDACI (in this example, BA) mixture caused a cytostatic effect manifested as proliferation arrest but not cell mortality.

Example 7

Cellular Maturation Induced by a Compound of Formula (I-a)

Figure 7:
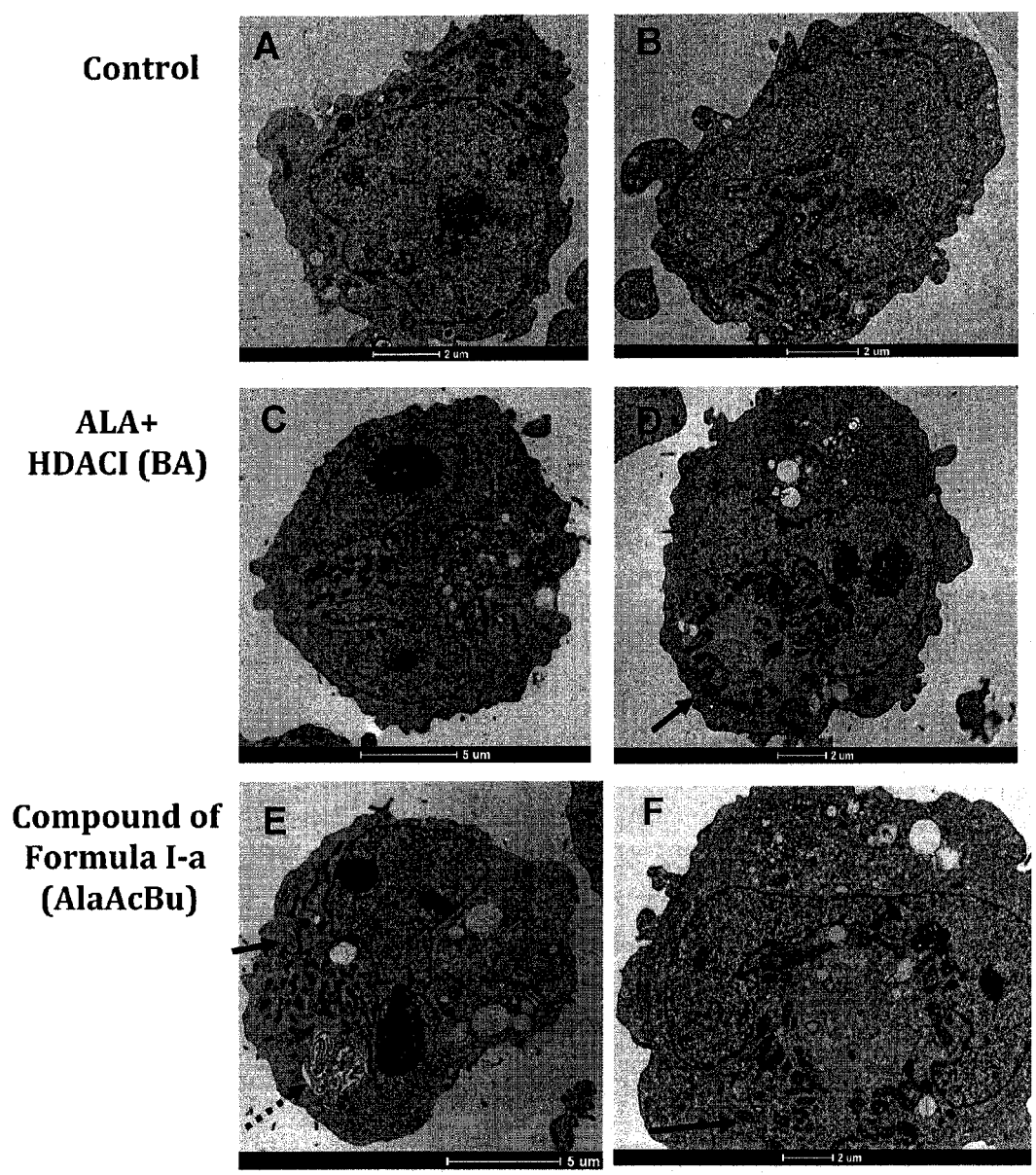
FIG. 7 shows TEM pictogrpahs of cells under various experimental conditions. Panels A-B, control; Panels C-D: cells treated with BA; Panels E-F: cells treated with AlaAcBu. Solid arrows: central stacking of mitochondria; dashed arrows: multiple vacuolar system preceding nuclear extrusion.

To evaluate morphologic changes associated with the effect of compound of formula (I-a) (in this example, AlaAcBu) and the ALA+HDACI (in this example, BA) mixture on K562 cells, the cells were examined by immunohystochemical experiments, as shown in FIG. 7. Typical ultrastructural changes induced by compound of formula (I-a) (in this example, AlaAcBu, panels E-F) and the ALA+HDACI (in this example, BA), panels C-D, identified by TEM included: chromatin condensation, cytosolic hemoglobinization (as shown for example, in FIG. 7, panels C-D), formation of multiple vacuolar system preceding nuclear extrusion (as shown for example, in FIG. 6, panel E, (dashed arrow)) and central stacking of mitochondria (as shown, for example, in FIG. 6 panels D, E and F, solid arrows).

Example 8

Figure 8A:
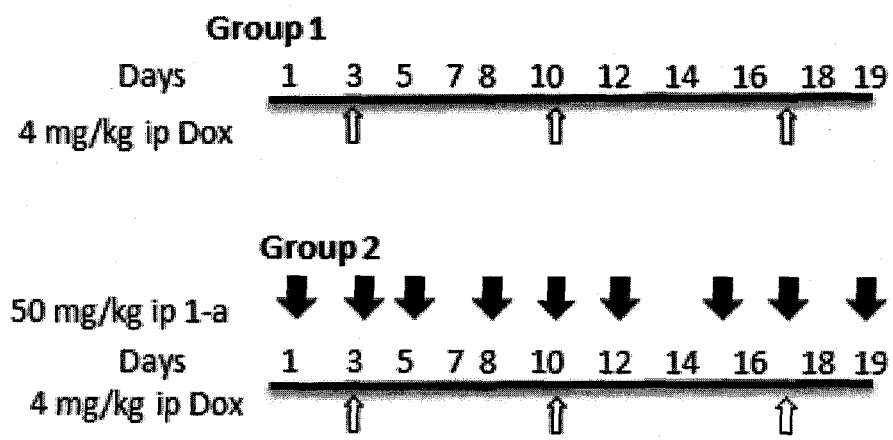
FIGS. 8A-B show results of in-vivo experiments testing the effect of compound of Formula (I-a) on Doxorubicin induced anemia in mice.
Figure 8B:
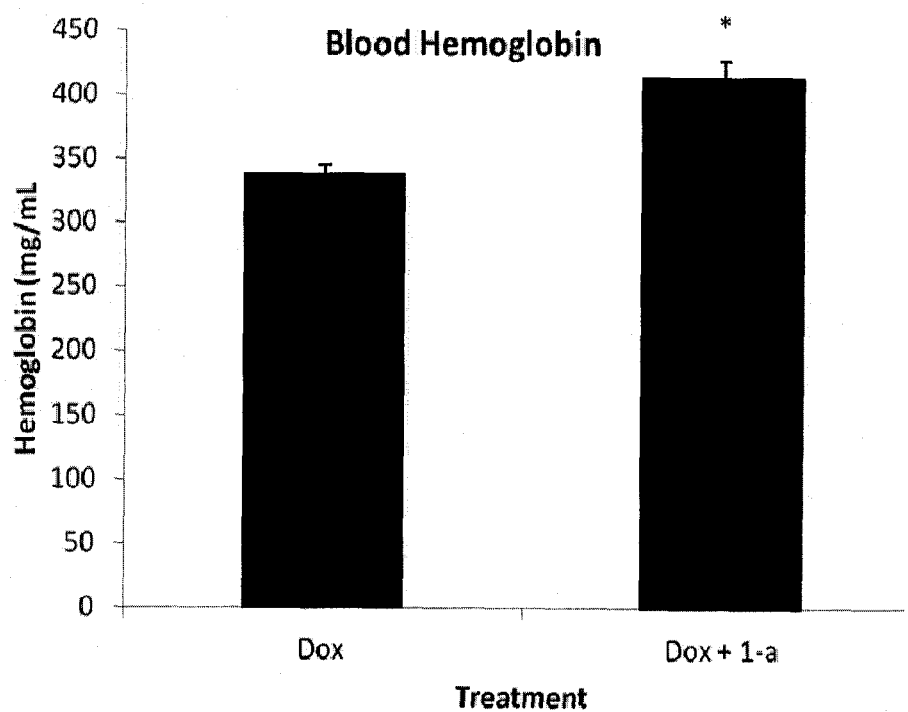

An In-Vivo Effect of Compounds of Formula (I-a) on Doxorubicin Induced Anemia in Mice In vivo 8 weeks old male Balb-c mice were divided to two groups, Group 1 received 4 mg/kg ip dose of doxorubicin (Dox) once a week and Group 2 received the same Dox treatment and in addition the mice were treated with 50 mg/kg ip dose of compound of formula (I-a) (in this example, 1-(butyryloxy)ethyl-5-amino-4-oxopentanoate, (AlaAcBu)) three times a week. A scheme of the protocol of this experiment is shown in FIG. 8A. The experiment was terminated on day 19, blood samples were drawn by retro-orbital venipuncture under anesthesia. Hemoglobin levels in heparinized whole blood were determined using Drabkin's reagent and standard hemoglobin obtained from Sigma-Aldrich and prepared and stored as instructed by the manufacturer. As shown in the bar graphs illustrated in FIG. 8B, the mice in Group 1 that were only treated with Dox had a significantly lower level of hemoglobin in their blood as compared to the Group 2 mice, which were administered with 50 mg/kg i.p. doses of a compound of formula (I-a) (in this example, (AlaAcBu)) twice a week, in addition to the Dox treatment. The results demonstrate that treatment with a compound of Formula (I-a) can ameliorate the Dox-induced suppression of erythropoiesis, in-vivo.

Example 9

Effect of Various Co-Drugs of Formula (I) and PDT on Intracellular Reactive Oxygen Species (ROS) Levels in Cancer Cells U251 cells are incubated for 4 hours with 0.25 mM of any one of the following: 5-ALA, an acyloxymethyl ester co-drug of formula (I); or acyloxyalkyl ester co-drugs of formula (I). Thereafter, half of the samples are irradiated for 10 min (12.5

J/cm$^2$). One hour after irradiation, ROS is measured by the FL-1 channel of FACS Calibur, using the DCF-DA dye.

Example 10

Effect of Various Co-Drugs of Formula (I) and PDT on Mitochondrial Membrane Potential and Mitochondrial Activity U251 cells are treated with the indicated compounds for 4 hours with 0.25 mM of any one of the following: 5-ALA, an acyloxymethyl ester co-drug of formula (I); or acyloxyalkyl ester co-drugs of formula (I), and irradiated. Mitochondrial activity is evaluated by MTT assay 24 hours after light irradiation (12 J/cm$^2$). The cells are further irradiated at differing light doses and the mitochondrial activity is evaluated by MTT assay 24 hours after light irradiation. The mitochondrial membrane potential of the cells is determined by staining with JC-1 immediately after irradiation (12 J/cm$^2$). Photographs of the cells are taken with a Nikon TE200-E fluorescence microscope (Tokyo, Japan) using an excitation filter of 450 nm and a barrier filter at 520 nm.

Example 11

Characterization of Cell Death Induced by Various Co-Drugs of Formula (I)

U251 cells are exposed to 0.25 mM of any one of the following: 5-ALA, an acyloxymethyl ester co-drug of formula (I); or acyloxyalkyl ester co-drugs of formula (I). The samples are irradiated for 10 min after 4 hours treatment. After 24 hours the cells are double-stained with Annexin V-FITC and PI and analyzed by FACS. One hour after irradiation, the cells are stained with May Grunwald and Giemsa and observed under light microscope-Nikon TE200-E.

Example 12

Cell Morphology of Cancer Cells Treated with Various Co-Drugs of Formula (I)

U251 cells are incubated for 4 hours with 0.25 mM of any one of the following: 5-ALA, an acyloxymethyl ester co-drug of formula (I); or acyloxyalkyl ester co-drugs of formula (I), followed by light irradiation for 10 min. Cell morphology is examined after 24 hours by SEM and TEM electron microscopy.

Example 13

Proteasome Activity of Cancer Cells Treated with Various Co-Drugs of Formula (I)

U251 cells are treated for 4 hours with 0.25 mM of any one of the following: 5-ALA, an acyloxymethyl ester co-drug of formula (I); or acyloxyalkyl ester co-drugs of formula (I). Half of the samples are irradiated at light intensity 6.5 J/cm$^2$. One hour later, whole cell extracts (40 µg of protein/lane) are loaded and resolved on 12% SDS gel, and Western blot analysis is performed. The expression level of the proteins is tested with the appropriate mouse/rabbit antibody for each protein. The chemotrypsin-like activity of the proteasome is measured in the treated cells and compared to that of untreated control cells. The caspase-like activity of the proteasome is measured in the treated cells and compared to that of untreated control cells.

Example 14

Direct Effect of Octanoic Acid on Cellular HDAC Activity

Figure 9A:
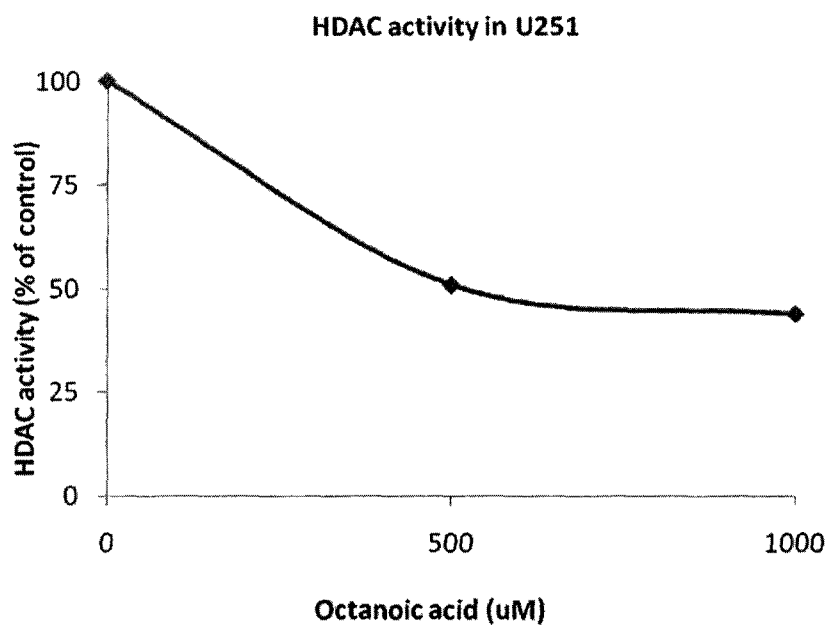
FIGS. 9A-B show line graphs demonstrating the effect of octanoic acid on the activity of HDAC.
Figure 9B:
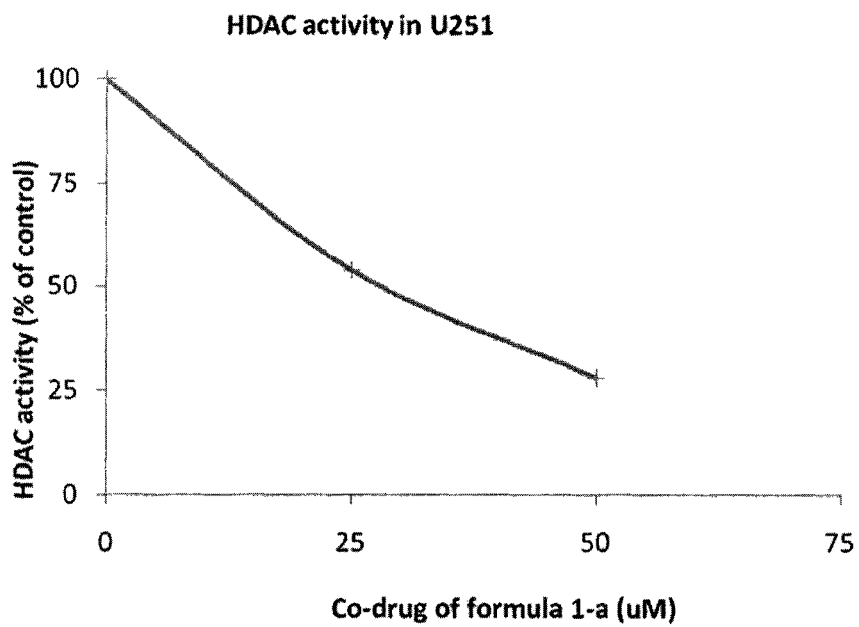

In order to test the direct effect of octanoic acid, as well as co-drugs of formula (I-a) (which comprise octanoic acid as the carboxylic acid), on the activity of cellular HDAC, the activity of HDAC is evaluated by incubating U-251 cells for 2 hours with the cell-permeable HDAC fluorometric substrate for HDAC class I and II (Fluor de Lys™), as detailed above. The results, which are presented in FIG. 9A, show that octanoic acid inhibits HDACs of classes I and II with an IC50 of 500 µM±20. As shown in FIG. 9B, incubating the cells with a co-drug of formula (I-a), inhibited the HDAC activity at IC50=35±3. The results presented in FIGS. 9A-B, demonstrate that octanoic acid is an HDACI. Additionally, the results presented in FIG. 9B demonstrate that the potency of the compound of formula (I-a) comprising octanoic acid is higher than the potency of the octanoic acid alone.

REFERENCES

1. Inoue H, Kajimoto Y, Shibata M A et al (2007) Massive apoptotic cell death of human glioma cells via a mitochondrial pathway following 5-aminolevulinic acid-mediated photodynamic therapy. J Neuro-oncol 83:223-231.
2. Amo T, Kawanishi N, Uchida M et al (2009) Mechanism of cell death by 5-aminolevulinic acid-based photodynamic action and its enhancement by ferrochelatase inhibitors in human histiocytic lymphoma cell line U937. Cell Biochem Funct 27:503-515.
3. Oliva Encina J, Rioja Sanz C (2009) Photodynamic diagnosis (PDD) in non-muscle invasive bladder cancer. Actas Urol Esp 33(9):965-975.
4. Fonseca R, Vianna L, Langeb N, Guyc R, Lopes M, Bentleya B (2004) Photodynamic therapy of skin cancer: controlled drug delivery of 5-ALA and its esters. Adv Drug Deliver Rev 56:77-94.
5. Berkovitch G, Doron D, Nudelman A, Malik Z, Rephaeli A (2008) Novel multifunctional acyloxyalkyl ester prodrugs of 5-aminolevulinic acid display improved anticancer activity independent and dependent on photoactivation. J Med Chem 51:7356-7369.
6. Xu W S, Parmigiani R B, Marks P A (2007) Histone deacetylase inhibitors: molecular mechanisms of action. Oncogene 26: 5541-5552.
7. Rephaeli A, Rabizadeh E, Aviram A, Shaklai M, Ruse M, et al. (1991) Derivatives of butyric acid as potential anti-neoplastic agents. Int J Cancer 49: 66-72.
8. Nudelman A, Ruse M, Aviram A, Rabizadeh E, Shaklai M, et al. (1992) Novel anticancer prodrugs of butyric acid. 2. J Med Chem 35:687-694.
9. Nudelman A, Levovich I, Cutts S M, Phillips D R, Rephaeli A (2005) The role of intracellularly released formaldehyde and butyric acid in the anticancer activity of acyloxyalkyl esters. J Med Chem 48:1042-1054.
10. Rephaeli A, Zhuk R, Nudelman A (2000) Prodrugs of butyric acid from bench to bedside: synthetic design, mechanisms of action and clinical applications. Drug Develop Res 50: 379-390.
11. Blank-Porat D, Gruss-Fischer T, Tarasenko N, Malik Z, Nudelman A, et al. (2007). The anticancer prodrugs of butyric acid AN-7 and AN-9, possess antiangiogenic properties. Cancer Letters 256: 39-48.

12. Rephaeli A, Entin-Meer M, Angel D, Tarasenko N, Gruss-Fisher T, et al. (2006) The selectivity and anti-metastatic activity of oral bioavailable butyric acid prodrugs. Invest. New Drugs 24: 383-392.
13. Mean R T, Jr. Advances in the anemia of chronic disease. 1999 Int. J. Hematol, 70: 7-11.
14. Griggs J J, Bumberg N. Recombinant EPO and blood transfusions in cancer chemotherapy-induced anemia. Anticancer Drugs 1998, 10: 925-32.
15. Grunberg-Etkovitz N, Greenbaum L, Grinblat B, Malik Z (2006) Proteasomal degradation regulates expression of porphobilinogen deaminase (PBGD) mutants of acute intermittent porphyria. Biochim Biophys Acta 1762:819-827.
16. Berkovitch G, Nudelman A, Ehenberg B, Rephaeil A and Malik Z. (2010). ALA-Butyrate prodrugs for Photo-Dynamic Therapy. LASER FLORENCE 2009: a gallery through the laser medicine world. Book Series: AIP Conference Proceedings, Volume 1226, Pages: 45-51. (23rd International Congress on Laser MedicineI-IALMS Courses/3rd Biannual Congress of the International-Photo-Therapy-Association, Nov. 6-7, 2009 Florence, ITALY).
17. Malik Z, Lugaci H. (1987). Destruction of erythroleukaemic cells by photoactivation of endogenous porphyrins. Br J. Cancer, 56:589-95.

What is claimed is:

1. A method for inducing erythropoiesis or for the treatment of anemia, comprising the step of administering to a subject in need thereof a compound represented by the structure of formula (I-a), or a pharmaceutical composition comprising such compound

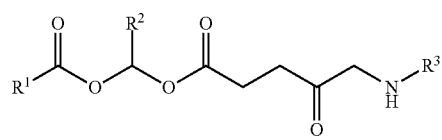

(I-a)

wherein $R^1$ is (a) a $C_1$-$C_{20}$ straight, branched, saturated or unsaturated or cyclic alkyl, wherein said alkyl may be unsubstituted or substituted with a phenyl, halogen, or oxygen;

(b) —$CH_2CH_2$—CO—$CH_2$—NH—$R_3$; or (c) —CH(NHCOCH$_3$)CH$_2$—SH;

$R^2$ is a $C_1$-$C_{20}$ straight, branched, saturated or unsaturated, or cyclic alkyl, wherein said alkyl may be unsubstituted or substituted with a phenyl, halogen, or oxygen; and $R^3$ is H or a nitrogen protecting group;

or a pharmaceutically acceptable salt thereof including salts, polymorphs, optical isomers, geometrical isomers, enantiomers, diastereomers, and mixtures thereof.

2. The method according to claim 1, wherein $R^1C(=O)$—O— is derived from a carboxylic acid selected from the group consisting of pivalic, butyric, valeric, hexanoic, heptanoic, octanoic, decanoic, 4-phenylbutyric, 4-phenylacetic and retinoic acid.

3. The method according to claim 1, wherein $R^2$—(CH)—O— is derived from an aldehyde of formula $R^2$—C(=O)H, wherein $R^2$ is as defined in claim 1.

4. The method according to claim 3, wherein the aldehyde is selected from the group consisting of formaldehyde, acetaldehyde, propionaldehyde and butyraldehyde.

5. The method according to claim 1, which is represented by the structure of formula (A), (B), (C), (D), (E), (F) or (G):

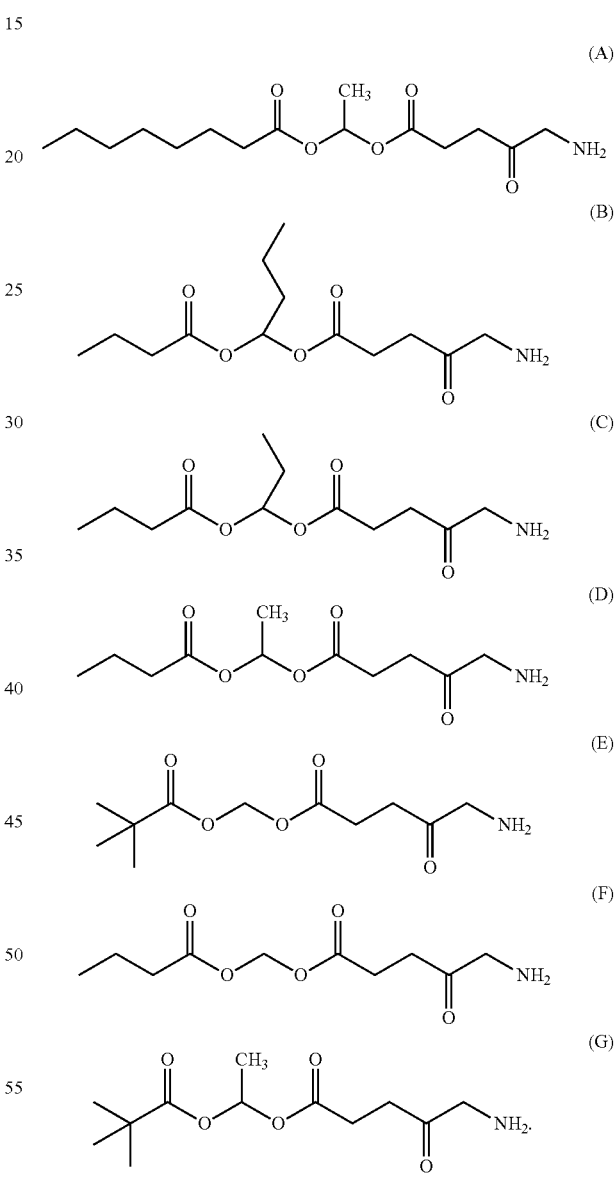

6. The method according to claim 1, wherein the compound represented by Formula (I-a) is in the form of an acid addition salt, wherein the salt is derived from a pharmaceutically acceptable acid selected from the group consisting of hydrochloric, hydrobromic, sulfuric, methane sulfonic, benzene sulfonic, naphthalene sulfonic, acetic, tartaric, maleic and malic acid, preferably wherein the acid is hydrochloric acid.

7. The method according to claim 1, wherein the pharmaceutical composition is in a form suitable for oral administration, intravenous administration by injection, topical administration, dermatological administration, administration by inhalation, or administration via a suppository.

8. A compound represented by the structure of formula (I):

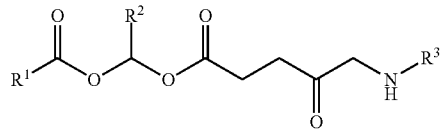

wherein

R¹ is (a) a $C_1$-$C_{20}$ straight, branched, saturated or unsaturated or cyclic alkyl, wherein said alkyl may be unsubstituted or substituted with a phenyl, halogen, or oxygen;

(b) —CH₂CH₂—CO—CH₂—NH—R₃; or (c) —CH(NHCOCH₃)CH₂—SH;

R² is H or a $C_1$-$C_{20}$ straight, branched, saturated or unsaturated, or cyclic alkyl, wherein said alkyl may be unsubstituted or substituted with a phenyl, halogen, or oxygen; and R³ is H or a nitrogen protecting group;

or a pharmaceutically acceptable salt thereof;

with the proviso that when R¹COO is derived from pivalic, butyric or valproic acid, R² is not H or CH₃;

including salts, polymorphs, optical isomers, geometrical isomers, enantiomers, diastereomers, and mixtures thereof.

9. The compound according to claim 8, wherein R¹C(=O)—O— is derived from a carboxylic acid selected from the group consisting of pivalic, butyric, valeric, hexanoic, heptanoic, octanoic, decanoic, 4-phenylbutyric, 4-phenylacetic and retinoic acid.

10. The compound according to claim 8, wherein R²—(CH)—O— is derived from an aldehyde of formula R²C(=O)H, wherein R² is as defined in claim 4.

11. The compound according to claim 10, wherein the aldehyde is selected from the group consisting of formaldehyde, acetaldehyde, propionaldehyde and butyraldehyde.

12. The compound according to claim 8, wherein R³ is H.

13. The compound according to claim 8, wherein R³ is a nitrogen protecting group selected from Boc and Cbz.

14. The compound according to claim 8, which is represented by the structure of formula (A), (B) or (C):

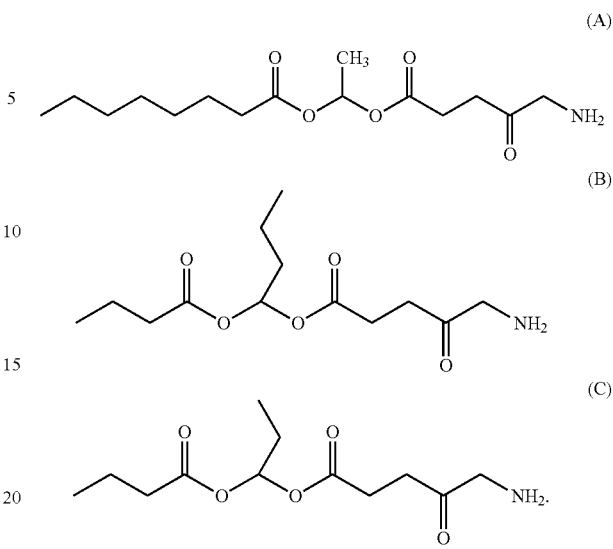

15. The compound according to claim 4, wherein the compound is in the form of an acid addition salt, wherein, the salt is derived from a pharmaceutically acceptable acid selected from the group consisting of hydrochloric, hydrobromic, sulfuric, methane sulfonic, benzene sulfonic, naphthalene sulfonic, acetic, tartaric, maleic and malic acid, preferably wherein the salt is a hydrochloric acid salt.

16. A pharmaceutical composition comprising a compound according to claim 8, and a pharmaceutically acceptable carrier or excipient.

17. The pharmaceutical composition according to claim 16, wherein the composition is in a form suitable for oral administration, intravenous administration by injection, topical administration, dermatological administration, administration by inhalation, or administration via a suppository.

18. A method for the treatment of cancer, comprising the step of administering to a subject in need thereof a pharmaceutical composition according to claim 17.

19. The method according to claim 18, wherein the treatment of cancer is selected from photodynamic therapy (PDT), non-photodynamic therapy (non-PDT), or a combination thereof.

20. The method according to claim 19, wherein R² is H, and the cancer treatment comprises non-photodynamic therapy (non-PDT).

21. The method according to claim 19, wherein R² is a $C_1$-$C_{20}$ straight, branched, saturated or unsaturated, or cyclic alkyl, and the cancer treatment comprises photodynamic therapy (PDT).

\* \* \* \* \*

```
                        SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
ccgacaagac caacgtca                                                   18

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
cgaagtgcgg gaagtagg                                                   18

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
acgagcagca ggagttca                                                   18

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
atgtcctggt ccttggct                                                   18

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
ctttggtatc gtggaaggac tc                                              22
```

```
<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
agtagaggca gggatgatgt tc                                          22
```